(12) United States Patent
Hechler et al.

(10) Patent No.: US 7,238,827 B2
(45) Date of Patent: Jul. 3, 2007

(54) PREPARATION OF AT LEAST ONE PARTIAL OXIDATION AND/OR AMMOXIDATION PRODUCT OF PROPYLENE

(75) Inventors: Claus Hechler, Ludwigshafen (DE); Götz-Peter Schindler, Mannheim (DE); Jochen Petzoldt, Mannheim (DE); Christoph Adami, Weinheim (DE); Otto Machhammer, Mannheim (DE); Klaus Joachim Müller-Engel, Stutensee (DE); Hans Martan, Frankenthal (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 470 days.

(21) Appl. No.: 10/465,659

(22) Filed: Jun. 20, 2003

(65) Prior Publication Data

US 2004/0063989 A1   Apr. 1, 2004

(30) Foreign Application Priority Data

Sep. 27, 2002 (DE) ............... 102 45 585
Oct. 1, 2002 (DE) ............... 102 46 119

(51) Int. Cl.
C07C 253/24 (2006.01)
C07C 27/10 (2006.01)
C07C 51/215 (2006.01)

(52) U.S. Cl. .......... 558/320; 562/512.2; 562/532; 562/545

(58) Field of Classification Search ......... 562/545, 562/512.2, 532; 558/320
See application file for complete search history.

(56) References Cited

U.S. PATENT DOCUMENTS

| 3,798,283 A | 3/1974 | Bitar et al. |
| 3,865,873 A | 2/1975 | Oda et al. |
| 4,066,704 A | 1/1978 | Harris et al. |
| 4,077,912 A | 3/1978 | Dolhyj et al. |
| 5,218,146 A | 6/1993 | Takata et al. |
| 5,268,497 A | 12/1993 | Ramachandran |
| 5,380,933 A | 1/1995 | Ushikubo et al. |
| 5,705,684 A | 1/1998 | Hefner et al. |
| 6,492,548 B1 | 12/2002 | Brockwell et al. |

FOREIGN PATENT DOCUMENTS

| DE | 2 058 054 | 6/1971 |
| DE | 2 251 364 | 5/1973 |
| DE | 2 351 151 | 4/1974 |
| DE | 35 21 458 | 12/1985 |
| DE | 195 30 454 | 2/1997 |
| DE | 100 51 419 | 4/2002 |
| DE | 101 22 027 | 5/2002 |
| DE | 101 19 933 | 10/2002 |
| DE | 101 31 297 | 1/2003 |
| EP | 0 117 146 | 8/1984 |
| EP | 0 293 224 | 11/1988 |
| EP | 0 372 972 | 6/1990 |
| EP | 0 529 853 | 3/1993 |
| EP | 0 608 838 | 8/1994 |
| EP | 0 731 077 | 9/1996 |
| EP | 0 938 463 | 9/1999 |
| EP | 1 192 987 | 4/2002 |
| GB | 2 160 543 | 12/1985 |
| WO | WO 00/20404 | 4/2000 |
| WO | WO 01/96270 | 12/2001 |
| WO | WO 01/96271 | 12/2001 |

*Primary Examiner*—James O. Wilson
*Assistant Examiner*—Ebenezer Sackey
(74) *Attorney, Agent, or Firm*—Oblon, Spivak, McClelland, Maier & Neustadt, P.C.

(57) ABSTRACT

Process for preparing at least one partial oxidation and/or ammoxidation product of propylene, in which the propylene is produced from crude propane by dehydrogenation and is subjected to a heterogeneously catalyzed gas-phase partial oxidation and/or partial gas-phase ammoxidation in the presence of unreacted propane as constituent of a gas mixture 2 containing <1% by volume of 1-butene.

73 Claims, No Drawings

PREPARATION OF AT LEAST ONE PARTIAL OXIDATION AND/OR AMMOXIDATION PRODUCT OF PROPYLENE

The present invention relates to a process for preparing at least one partial oxidation and/or ammoxidation product of propylene, in which a) crude propane is subjected to a homogeneously and/or heterogeneously catalyzed dehydrogenation and/or oxydehydrogenation in the presence and/or absence of oxygen in a first step to produce a gas mixture 1 comprising propane and propylene, and b) part of the constituents other than propane and propylene present in the gas mixture 1 formed in the first step is, if appropriate, separated off from the gas mixture 1 and/or converted into other compounds so as to produce a gas mixture 1' comprising propane and propylene and also compounds other than oxygen, propane and propylene from the gas mixture 1 and, in at least one further step, c) gas mixture 1 and/or gas mixture 1' are/is subjected as constituent of a gas mixture 2 to a heterogeneously catalyzed gas-phase partial oxidation and/or partial gas-phase ammoxidation of propylene present in gas mixture 1 and/or gas mixture 1'.

For the purposes of the present text, crude propane is a propane-containing gas which comprises not only propane and possibly propylene but also at least one, frequently at least two or three and often at least four or five, chemical compound(s) other than propane and propylene. Such chemical compounds can be detected chromatographically, e.g. gas-chromatographically, in crude propane.

For the purposes of the present text, an oxydehydrogenation of propane is a dehydrogenation which is forced by oxygen present and in which no free hydrogen is formed or is detectable as an intermediate. In contrast to conventional dehydrogenation, which proceeds endothermically, oxydehydrogenation is exothermic. The oxydehydrogenation of propane can be carried out at elevated temperatures in the presence of homogeneous catalysts (i.e. without the presence of a, for example, solid catalyst; cf., for example, U.S. Pat. No. 3,798,283) or heterogeneous catalysts (e.g. over solid catalysts; cf. DE-A 2058054 and DE-A 19530494).

The same is essentially true of conventional dehydrogenation, in which the dehydrogenation step is carried out without active involvement of oxygen (cf., for example, EP-A 731 077 and WO 01/96270). In this case, hydrogen is formed as primary by-product instead of the water formed in the case of oxydehydrogenation.

For the purposes of the present text, complete oxidation of propylene is conversion of all the carbon present in the propylene into oxides of carbon (CO, $CO_2$). All other reactions of propylene with molecular oxygen are encompassed by the term "partial oxidation" in this text. The additional involvement of ammonia in the reaction characterizes ammoxidation.

The preferred partial oxidation and/or ammoxidation products of propylene are, for the purposes of the present text, acrolein, acrylic acid, propylene oxide and acrylonitrile.

Partial oxidation and/or ammoxidation products of propylene are important intermediates, e.g. for the preparation of polymers.

Such partial oxidations and/or ammoxidations are carried out by methods known per se (the amount of ammonia present in the reaction gas mixture can be controlled in a manner known per se to give a reaction which is essentially exclusively a partial oxidation or exclusively a partial ammoxidation or is a superposition of the two reactions). These are heterogeneously catalyzed gas-phase reactions over solid, in general oxidic, catalysts.

DE-A 2 351 151 (example of the conversion of propylene into acrolein and/or acrylic acid and of propylene into acrylonitrile) and EP-A 372 972 (example of the conversion of propylene into propylene oxide) may be cited by way of example.

As oxidant, use is normally made of molecular oxygen which may, for example, be added in pure form or in admixture with gases which are essentially inert in the partial oxidation/ammoxidation (e.g. as air) to the reaction gas mixture. The reactants in the reaction gas mixture are frequently also diluted by at least one inert gas (e.g. $N_2$, $H_2O$, CO, $CO_2$, saturated hydrocarbons, e.g. $C_1$–$C_5$-hydrocarbons (e.g. as described in DE-A 1924431 and EP-A 293224), He and/or Ar etc.) to aid heat removal and to make the reaction safe. DE-B 2251364 recommends, inter alia, the use of butane as inert diluent gas. As mentioned above, ammoxidation is distinguished by the additional presence of ammonia.

Unlike the case of laboratory and pilot plant experiments, the starting propylene used on an industrial scale is usually not chemically pure propylene but instead a crude propylene which contains impurities but nevertheless has a comparatively high purity (e.g. "polymer grade" or "chemical grade"; cf. DE-A 10131297).

The isolation of such comparatively pure crude propylene is relatively complicated and expensive. It normally starts from crude paraffinic hydrocarbons and generally comprises at least one purification step in which unreacted paraffinic hydrocarbon is separated off from the propylene formed by means of physical methods (cf., for example, DE-A 3 521 458). The purification step or steps usually comprise(s) a removal of olefins other than propylene and of other by-products different from propylene, including the secondary components originally present in the crude paraffinic hydrocarbon.

The abovementioned separations generally require a high capital investment and, as a result of the similarity of olefinic/paraffinic hydrocarbons, are very energy-intensive. They are therefore usually only employed in conjunction with refinery crackers and steam crackers and are only worthwhile because the major part of the crude propylene obtained in this way is required in large quantities ("economy of scale") for subsequent polymerizations (e.g. preparation of polypropylene) and, in addition, experiences an increase in value as a result.

The proportion of these crude propylenes going into partial oxidations and/or ammoxidations is of subordinate importance and is effectively a secondary demand, which is why crude propylene produced in such a way still has an acceptable raw materials price for partial oxidations and/or ammoxidations.

This raw materials price could be reduced appreciably only if it were possible to omit part or all of the separations referred to.

As a solution to this problem, EP-B 938463 proposes partially dehydrogenating crude propane, for example, in the presence of oxygen and heterogeneous catalysts in a first step to produce a first gas mixture comprising propylene and propane which is subjected as such, i.e. without intermediate treatment, as constituent of a second gas mixture to a heterogeneously catalyzed gas-phase partial oxidation of propylene present in the first gas mixture to acrolein and/or acrylic acid.

On the question of the purity of the crude propane to be used, EP-B 938463 states in column 3, line 40 ff, that: "The purity of the starting material alkane is not particularly limited." "Further, the starting material alkane may be a mixture of various alkanes. Typically the feed will comprise at least 30 mole percent, preferably at least 50 mole percent and more preferably at least 80 mole percent propane. The source of the alkane, e.g. propane feed, for use in the process of the present invention is not critical."

Furthermore, EP-B 938463 teaches in column 3, line 17 ff: "Hence, after recovery of the acrolein, the noncondensed gases containing propane may be recycled without significant, additional purification steps."

The teachings of EP-A 117146 correspond essentially to those of EP-B 938463, except that EP-A 117146 recommends carrying out the heterogeneously catalyzed dehydrogenation of propane with exclusion of oxygen.

Furthermore, EP-A 117146 teaches on page 11, line 14 ff, on the subject of the abovementioned recycle stream: "Since the light and heavy hydrocarbon by-products, such as methane, ethane, ethylene, butane, and butenes boil at temperatures significantly different from those of acrolein or the $C_3$ hydrocarbons, they may be separated by distillation. Alternatively, streams containing the by-products in concentrated amounts may be purged." The possibility of such a purge stream of recycled gas is also envisaged in EP-B 938463 in column 11, line 10.

The necessity of separating off the abovementioned secondary components prior to the partial oxidation and/or ammoxidation is not recognized in either document.

The teachings of WO 01/96270 follow on from the teachings of EP-B 938463 and EP-A 117 146. Thus, it states on page 4, line 10 ff, that: "The feed gas mixture to the oxidation stage B in the process of the invention can of course further comprise, in addition to the constituents mentioned above, other constituents such as CO, $CO_2$, $H_2O$, noble gases such as He and/or Ar, hydrogen, methane, ethylene, butanes, butenes, butynes, pentanes, propyne, allenes and/or acrolein."

Furthermore, WO 01/96270 teaches on page 15, line 26 ff, in respect of the crude propane to be used for the dehydrogenation step: "It is important for the purposes of the invention that the propane used in stage A does not have to be pure propane. Rather, the propane used can contain up to 50% by volume of other gases such as ethane, methane, ethylene, butanes, butenes, propyne, acetylene, $H_2S$, $SO_2$, pentanes, etc."

Although wo 01/96270 also recommends separating off at least part of the hydrogen present in the first gas mixture formed in the dehydrogenation step and comprising propane and propylene before this first gas mixture is used further for the partial oxidation of the propylene present therein and, in the course of this separation, optionally separating off other, if desired essentially all, constituents other than propane and propylene, and EP-B 731077 regards quantitative removal of all constituents other than propane, propylene and possibly molecular oxygen from such a first gas mixture before it is used further as particularly preferred, any separation process to be used for this purpose adversely affects the economics of the overall process and, secondly, some of the processes recommended in the abovementioned documents for such a quantitative separation are found to be relatively unsuitable. The latter applies, for example, to the absorption/desorption process recommended in WO 01/96270 on page 16, bottom, which on closer examination has been found to be relatively unsuitable for separating, for example, $C_4$-hydrocarbons from $C_3$-hydrocarbons.

The necessity of separating off particular secondary components after the dehydrogenation and/or oxydehydrogenation step or even before this step in order to reduce the formation of by-products in addition to the formation of the desired target product in the oxidation and/or ammoxidation step or steps when changing from crude propylene to crude propane as raw material is not recognized in the cited prior art. Although the prior art is conscious of the alteration in by-product formation with the raw material change (according to WO 01/96270, the presence of propane, for example, in the partial oxidation causes increased formation of propionaldehyde and/or propionic acid; however, the advantage of not separating off the propane from the propylene formed in the dehydrogenation is not accorded greater importance), this is not considered particularly critical since a preliminary separation is generally more complicated than the separation of target product and by-product. This is also considered in the light of the background that a target product separation from by-products formed has to be carried out in any case.

This opinion is quite obviously also shared by those, for example, EP-A 1192987, DE-A 10122027, EP-A 608838, EP-A 529853, DE-A 10051419 or DE-A 10119933, who recommend carrying out the process defined at the beginning of this text in a single reaction zone (it is usually carried out in at least two reaction zones) over a catalyst charge whose active oxide composition consists of at least one multimetal oxide comprising the elements Mo, V and Te and/or Sb. The basis of this procedure is that the relevant active oxide composition is able to catalyze both the oxydehydrogenation of propane to propylene (cf., for example, EP-B 938463, column 4, line 37 ff) and the partial oxidation and/or ammoxidation of propylene. It goes without saying that in such a procedure the gas mixture 1 is used as such for the subsequent partial oxidation and/or ammoxidation step or steps.

Nevertheless, EP-A 1192987, for example, recommends on page 9, line 26 ff: "Similarly, there is no limitation on the source of the alkane. It may be purchased, per se, or in admixture with an alkene and/or other impurities. Moreover, the alkane, regardless of source, and the alkene, regardless of source, may be blended as desired." Completely analogously, DE-A 10122027 teaches on page 3, lines 35/36: "No particularly high demands in terms of purity are placed on the propane to be used for the process of the invention." WO 0196271 likewise deems crude propanes of the most different degrees of purity to be useful.

A disadvantage of the above recommendations of the prior art is that they do not address the question of which constituents which may be present in inexpensive crude propane or chemical compounds (which are not present or present only in traces in the crude propylenes normally used, so that their adverse effects have hitherto remained unnoticed) which are formed during the course of the first step from such constituents and are then present in the first gas mixture act as catalyst poisons in the subsequent heterogeneously catalyzed partial oxidation and/or ammoxidation by reducing the activity and/or selectivity of the catalyst in respect of the desired partial oxidation and/or ammoxidation of propylene.

As a result of detailed and careful studies, it has now been found that $C_4$-hydrocarbons (chemical compounds consisting of four carbon atoms and hydrogen) in general and among these especially the group of olefinic representatives (1-butene, trans-2-butene, cis-2-butene and isobutene) and among these in particular 1-butene form such catalyst poisons. However, the saturated representatives and the other unsaturated representatives also have adverse effects.

C$_4$-Hydrocarbons (e.g. n-butane, isobutane, trans-2-butene, cis-2-butene, isobutene, 1,3-butadiene, 1,2-butadiene, 1-butyne and/or 2-butyne) are, however, ubiquitous compounds accompanying propane and are therefore usually present in significant amounts in inexpensive crude propanes. This applies particularly to the saturated C$_4$-hydrocarbons from which at least some olefinic C$_4$-hydrocarbons, especially the particularly troublesome 1-butene, are invariably formed under the conditions of a partial dehydrogenation and/or oxydehydrogenation of propane.

It is an object of the present invention to provide a process of the type described at the outset for preparing at least one partial oxidation and/or ammoxidation product of propylene, which, unlike the processes of the prior art, takes account of the abovementioned facts.

We have found that this object is achieved by a process for preparing at least one partial oxidation and/or ammoxidation product of propylene, in which a) crude propane is subjected to a homogeneously and/or heterogeneously catalyzed dehydrogenation and/or oxydehydrogenation in the presence and/or absence of oxygen in a first step to give a gas mixture 1 comprising propane and propylene, and b) part of the constituents other than propane and propylene present in the gas mixture 1 formed in the first step is, if appropriate, separated off from the gas mixture 1 and/or converted into other compounds so as to produce a gas mixture 1' comprising propane and propylene and also compounds other than oxygen, propane and propylene from the gas mixture 1 and, in at least one further step, c) gas mixture 1 and/or gas mixture 1' are/is subjected as constituent of a gas mixture 2 to a heterogeneously catalyzed gas-phase partial oxidation and/or partial gas-phase ammoxidation of propylene present in gas mixture 1 and/or gas 45 mixture 1', wherein the 1-butene content of the gas mixture 2 is $\leq 1\%$ by volume.

The amount of the constituents other than propane and propylene that are removed from the mixture 1 and/or converted into other compounds on the route to gas mixture 1' can be in the process of the present invention up to 5% by weight or up to 10% by weight or up to 20% by weight or up to 30% or 40% by weight or up to 60% by weight or up to 70 or 80% by weight or up to 85 or 90% by weight or up to 94% by weight or up to 96 or 98% by weight or up to 99% by weight or more, based on the amount of these constituents which is present in gas mixture 1.

According to the present invention, the 1-butene content of gas mixture 2 is $\leq 0.9\%$ by volume or $\leq 0.75\%$ by volume or $\leq 0.6\%$ by volume or $\leq 0.5\%$ by volume or $\leq 0.4\%$ by volume, particularly preferably $\leq 0.3\%$ by volume, very particularly preferably $\leq 0.2\%$ by volume and more preferably $\leq 0.1\%$ by volume or $\leq 0.05\%$ by volume or $\leq 0.03\%$ by volume or $\leq 0.01\%$ by volume. In the case of gas mixtures 2 which no longer contain any 1-butene at all, this adverse effect of course no longer appears at all. However, in an overall assessment of the economics, it may be justifiable to accept some adverse effect of 1-butene in the gas mixture 2 and leave its content in the gas mixture 2 at values of $\geq 0.001\%$ by volume or $\geq 0.003\%$ by volume or $\geq 0.006\%$ by volume or in extreme cases $\geq 0.009\%$ by volume.

In the process of the present invention, the above-mentioned limits preferably do not apply only to the amount of 1-butene present in the gas mixture 2 but also at the same time, independently of one another, to each other possible representative of the butenes (i.e. trans-2-butene, cis-2-butene and isobutene), and very particularly preferably at the same time to the total amount of butenes in the gas mixture 2. This means that gas mixtures 2 suitable for the purposes of the present invention are, for example, those in which:

the 1-butene content is $\leq 1\%$ by volume and the total content of butenes is $\leq 1\%$ by volume; or the 1-butene content is $\leq 0.5\%$ by volume and the total content of butenes is $\leq 1\%$ by volume; or the 1-butene content is $\leq 0.3\%$ by volume and the total content of butenes is $\leq 1\%$ by volume; or the 1-butene content is $\leq 0.5\%$ by volume and the total content of butenes is $\leq 0.75\%$ by volume; or the 1-butene content is $\leq 0.75\%$ by volume and the total content of butenes is $\leq 1\%$ by volume; or the 1-butene content is $\leq 0.4\%$ by volume and the total content of butenes is $\leq 1\%$ by volume; or the 1-butene content is $\leq 0.2\%$ by volume and the total content of butenes is $\leq 1\%$ by volume; or the 1-butene content is $\leq 0.5\%$ by volume and the total content of butenes is $\leq 0.5\%$ by volume; etc.

The process of the present invention offers essentially two possible ways of adhering to the abovementioned limits; of these, it is possible to employ either only one or both.

Firstly, the starting material can be a crude propane which either contains no C$_4$-hydrocarbons at all or which contains only such amounts of C$_4$-hydrocarbons that the limits specified according to the present invention for the contents of 1-butene, (total) butenes and (total) C$_4$-hydrocarbons in the gas mixture 2 are adhered to. What content of which of the possible C$_4$-hydrocarbons in the crude propane is compatible with the process of the present invention depends, inter alia, on the specific boundary conditions employed for the first step of the process and can be determined by a person skilled in the art in a few preliminary tests, in each case subject to these specific boundary conditions.

If it is necessary for C$_4$-hydrocarbons to be separated off from commercial crude propane, this can be carried out in a manner known per se, e.g. by rectification. It goes without saying that all other separation processes such as adsorption/desorption (e.g. pressure swing adsorption), extraction and/or absorption/desorption are also possible.

Additionally or alternatively, C$_4$-hydrocarbons in general and 1-butene or butenes in particular can be separated off from the gas mixture 1 so that the contents of these components are at or below the limits to be adhered to according to the present invention before the mixture is used further according to the present invention as gas mixture 1'. This measure is employed, for example, when the interfering C$_4$-hydrocarbons are formed, e.g. from propane, only during the course of the oxydehydrogenation or dehydrogenation step, e.g. by disproportionation and/or metathesis. The probability of this is increased, inter alia, when the partial gas recycle process of DE-A 10211275 is employed in the first step of the process of the present invention (in the case of a catalytic dehydrogenation). As separation methods, it is possible to employ, for example, the combination of absorption and desorption or stripping (preferably as pressure absorption) described in DE-A 10131297, pressure swing adsorption, rectification and/or extraction. In the case of stripping, it needs to be ensured that no C$_4$-hydrocarbons are introduced via the stripping gas used.

If the propane and propene present in enriched form in an absorption medium (e.g. after absorption from the product gas mixture from a catalytic dehydrogenation) is stripped out by means of air, one of the process scenarios according to the present invention can apply, viz. the gas mixture 1' produced by stripping can, if the amount of stripping gas is chosen appropriately, be used directly for the gas-phase partial oxidation and/or the partial gas-phase ammoxidation and is thus identical to the gas mixture 2. In this case, the content of components other than propane, propene and oxygen in the gas mixture 1' will generally be from 35 to 55% by volume. If acrolein and/or acrylic acid are/is to be prepared according to the present invention, such a procedure is preferred.

Of course, the removal of $C_4$-hydrocarbons as discussed above can also be accompanied by removal of other constituents different from propane and propylene. It is naturally also possible to separate off part of the propane and/or propylene in each case.

According to the present invention, the separation processes discussed are advantageously directed specifically at removal of the $C_4$-hydrocarbons in order to limit the total separation cost and thus the adverse effect on the economics.

This means that, under normal circumstances, a gas mixture 1' will, in the process of the present invention, still contain at least $\geq 0.1\%$ by volume, frequently $\geq 0.2\%$ by volume or $\geq 0.3\%$ by volume or $\geq 0.4\%$ by volume or $\geq 0.5\%$ by volume, often $\geq 0.6\%$ by volume or $\geq 0.8\%$ by volume or $\geq 1\%$ by volume, or $\geq 2\%$ by volume or $\geq 3\%$ by volume or $\geq 5\%$ by volume, quite possibly $\geq 10\%$ by volume or $\geq 15\%$ by volume or $\geq 20\%$ by volume or $\geq 25\%$ by volume or $\geq 30\%$ by volume or $\geq 35\%$ by volume, of constituents other than propane and propylene and oxygen.

Normally, however, the proportion of constituents other than propane and propylene and oxygen in the gas mixture 1' in the process of the present invention will be $\leq 80\%$ by volume or $\leq 70\%$ by volume or $\leq 60\%$ by volume or $\leq 50\%$ by volume or $\leq 40\%$ by volume.

According to the present invention, it is advantageous for the separations discussed above to be carried out so that the gas mixture 2 not only conforms to the 1-butene content and, if applicable, contents of other butene isomers and, if applicable, total butene contents which are suitable according to the present invention but at the same time has a total content of $C_4$-hydrocarbons of $\leq 3\%$ by volume or $\leq 2.5\%$ by volume, preferably $\leq 2\%$ by volume and very particularly preferably $\leq 0.5\%$ by volume or $\leq 0.3\%$ by volume or $\leq 0.1\%$ by volume. This is because the presence of $C_4$-hydrocarbons (in particular n-butane and/or isobutane) has been found to be quite generally disadvantageous in the partial oxidation and/or ammoxidation of propylene.

In the case of gas mixtures 2 which no longer contain any $C_4$-hydrocarbons at all, their adverse effect no longer shows up at all. However, in an overall assessment of economics, it can be justifiable to accept some adverse effect of the $C_4$-hydrocarbons in the gas mixture 2 and leave their total content in the gas mixture 2 at values of $\geq 0.05\%$ by volume or $\geq 0.07\%$ by volume or $\geq 0.09\%$ by volume or $\geq 0.1\%$ by volume or in extreme cases $\geq 0.2\%$ by volume.

This means that the objectives of the process of the present invention are achieved, in particular, when, for gas mixture 2, at least one of the limits imposed according to the present invention on the 1-butene content and at the same time one of the limits imposed in the present text on the total content of $C_4$-hydrocarbons are adhered to.

In other words, gas mixtures 2 which are suitable according to the present invention include, for example, those which meet one of the following pairs of specifications:

1-butene content $\leq 1\%$ by volume and total content of $C_4$-hydrocarbons $\leq 3\%$ by volume; or
1-butene content $\leq 1\%$ by volume and total content of $C_4$-hydrocarbons $\leq 2\%$ by volume; or
1-butene content $\leq 0.5\%$ by volume and total content of $C_4$-hydrocarbons $\leq 3\%$ by volume; or
1-butene content $\leq 0.5\%$ by volume and total content of $C_4$-hydrocarbons $\leq 2\%$ by volume; or
1-butene content $\leq 0.75\%$ by volume and total content of $C_4$-hydrocarbons $\leq 3\%$ by volume; or
1-butene content $\leq 0.75\%$ by volume and total content of $C_4$-hydrocarbons $\leq 2\%$ by volume; or
1-butene content $\leq 0.4\%$ by volume and total content of $C_4$-hydrocarbons $\leq 3\%$ by volume; or
1-butene content $\leq 0.4\%$ by volume and total content of $C_4$-hydrocarbons $\leq 2\%$ by volume; or
1-butene content $\leq 0.4\%$ by volume and total content of $C_4$-hydrocarbons $\leq 1\%$ by volume; or
1-butene content $\leq 0.3\%$ by volume and total content of $C_4$-hydrocarbons $\leq 3\%$ by volume; or
1-butene content $\leq 0.3\%$ by volume and total content of $C_4$-hydrocarbons $\leq 2\%$ by volume; or
1-butene content $\leq 0.3\%$ by volume and total content of $C_4$-hydrocarbons $\leq 1\%$ by volume; etc.

Gas mixtures 2 which at the same time meet at least one of the limits imposed in the present text on the total content of butenes in the gas mixture 2 are particularly advantageous in the process of the present invention.

In other words, gas mixtures 2 suitable for the purposes of the present invention include, in particular, those which meet one of the following pairs of specifications:

content of 1-butene $\leq 1\%$ by volume and total content of butenes $\leq 1\%$ by volume and total content of $C_4$-hydrocarbons $\leq 3\%$ by volume; or
content of 1-butene $\leq 0.75\%$ by volume and total content of butenes $\leq 1\%$ by volume and total content of $C_4$-hydrocarbons $\leq 3\%$ by volume; or
content of 1-butene $\leq 0.5\%$ by volume and total content of butenes $\leq 1\%$ by volume and total content of $C_4$-hydrocarbons $\leq 3\%$ by volume; or
content of 1-butene $\leq 0.3\%$ by volume and total content of butenes $\leq 1\%$ by volume and total content of $C_4$-hydrocarbons $\leq 3\%$ by volume; or
content of 1-butene $\leq 0.5\%$ by volume and total content of butenes $\leq 0.75\%$ by volume and total content of $C_4$-hydrocarbons $\leq 3\%$ by volume; or
content of 1-butene $\leq 0.5\%$ by volume and total content of butenes $\leq 0.5\%$ by volume and total content of $C_4$-hydrocarbons $\leq 3\%$ by volume; or
content of 1-butene $\leq 0.5\%$ by volume and total content of butenes $\leq 0.5\%$ by volume and total content of $C_4$-hydrocarbons $\leq 2\%$ by volume; etc.

Processes in which not only the abovementioned combinations of 1-butene content and total content of $C_4$-hydrocarbons and possibly total content of butenes in the gas mixture 2 are adhered to but at the same time a gas mixture 1' containing at least $\geq 0.1\%$ by volume or $\geq 0.2\%$ by volume or $\geq 0.3\%$ by volume or $\geq 0.4\%$ by volume or $\geq 0.5\%$ by volume or $\geq 0.6\%$ by volume or $\geq 0.8\%$ by volume or $\geq 1\%$ by volume or $\geq 2\%$ by volume or $\geq 3\%$ by volume or $\geq 5\%$ by volume or $\geq 10\%$ by volume or $\geq 15\%$ by volume or $\geq 20\%$ by volume or $\geq 25\%$ by volume or $\geq 30\%$ by volume (but usually $\leq 80\%$ by volume or $\leq 70$ by volume or $\leq 60\%$ by volume or $\leq 50\%$ by volume) of constituents other than propane and propylene and oxygen is used are particularly advantageous according to the present invention.

The studies carried out in the context of the present invention have also shown that it is generally advantageous in the process of the present invention for the propane content in the gas mixture 2 to be comparatively low in order to avoid undesirable total combustion of propylene in the partial oxidation and/or ammoxidation. According to the present invention, the propane content of the gas mixture 2 is preferably $\leq 60\%$ by volume or $\leq 50\%$ by volume. Propane contents of the gas mixture 2 of from 20 to 40% by volume, e.g. about 30% by volume, have been found to be particularly advantageous.

If any ammonia content employed in the case of nitrile production is disregarded (i.e. is also not taken into account in the basis for the % by volume), gas mixtures 2 suitable for the process of the present invention are therefore generally ones which, firstly, conform to the limits according to the present invention in respect of their 1-butene content, preferably additionally the total butene content and particularly preferably additionally the total $C_4$-hydrocarbon content, and, secondly, have the following contents:

from 7 to 15% by volume of $O_2$, from 5 to 10% by volume of propylene, from 15 to 40% by volume of propane, frequently from 25 to 35% by volume, from 25 to 60% by volume of nitrogen, frequently from 40 to 60% by volume, from 1 to 5% by volume of total CO, $CO_2$ and $H_2O$ and from 0 to 5% by volume of other constituents.

This applies particularly when the gas mixture 2 is used for a heterogeneously catalyzed partial oxidation of the propylene present in the gas mixture 2 for preparing acrolein and/or acrylic acid.

Otherwise, possible gas mixtures 2 for all heterogeneously catalyzed partial oxidations and/or ammoxidations of propylene encompassed by the process of the present invention include, in particular, those which, once again disregarding any $NH_3$ content for nitrile formation (also in the basis of the percentages), have the following composition:

| | |
|---|---|
| $H_2O$ | $\leq 60\%$ by volume, usually $\leq 20\%$ by volume, generally from 0 to 5% by volume; |
| $N_2$ | $\leq 80\%$ by volume, usually $\leq 70\%$ by volume, generally from 40 to 60% by volume; |
| $O_2$ | up to 20% by volume, usually from 2 to 20% by volume, generally from 5 to 15% by volume; |
| CO | $\leq 2\%$ by volume, usually $\leq 1\%$ by volume, generally from 0 to 0.5% by volume; |
| $CO_2$ | $\leq 5\%$ by volume, usually $\leq 3\%$ by volume, generally from 0 to 2% by volume; |
| ethane | $\leq 10\%$ by volume, usually $\leq 5\%$ by volume, generally from 0 to 2% by volume; |
| ethylene | $\leq 5\%$ by volume, usually $\leq 2\%$ by volume, generally from 0 to 0.5% by volume; |
| methane | $\leq 5\%$ by volume, usually $\leq 2\%$ by volume, generally from 0 to 0.2% by volume; |
| propane | $> 0$, $\leq 50\%$ by volume, usually from 10 to 50% by volume, generally from 20 to 40% by volume; |
| cyclopropane | $\leq 0.1\%$ by volume, usually $\leq 0.05\%$ by volume, generally from 0 to 150 ppm by volume; |
| propyne | $\leq 0.1\%$ by volume, usually $\leq 0.05\%$ by volume, generally from 0 to 150 ppm by volume; |
| propadiene | $\leq 0.1\%$ by volume, usually $\leq 0.05\%$ by volume, generally from 0 to 150 ppm by volume; |
| propylene | $> 0$, $\leq 30\%$ by volume, usually $\geq 2$, $\leq 20\%$ by volume, generally from 5 to 10% by volume; |
| $H_2$ | $\leq 30\%$ by volume, usually $\leq 20\%$ by volume, generally from 0 to 10% by volume; |
| isobutane | $\leq 3\%$ by volume, preferably $\leq 2\%$ by volume, frequently from 0.1 to 1% by volume; |
| n-butane | $\leq 3\%$ by volume, preferably $\leq 2\%$ by volume, frequently from 0.1 to 1% by volume; |
| trans-2-butene | $\leq 1\%$ by volume, preferably $\leq 0.5\%$ by volume, frequently $\geq 0.003\%$ by volume, $\leq 0.1\%$ by volume; |
| cis-2-butene | $\leq 1\%$ by volume, preferably $\leq 0.5\%$ by volume, frequently $\geq 0.003\%$ by volume, $\leq 0.1\%$ by volume; |
| 1-butene | $\leq 1\%$ by volume, preferably $\leq 0.5\%$ by volume, frequently $\geq 0.003\%$ by volume, $\leq 0.1\%$ by volume; |
| isobutene | $\leq 1\%$ by volume, preferably $\leq 0.5\%$ by volume, frequently $\geq 0.003\%$ by volume, $\leq 0.1\%$ by volume; |
| 1,3-butadiene | $\leq 1\%$ by volume, preferably $\leq 0.5\%$ by volume, frequently $\geq 0.003\%$ by volume, $\leq 0.1\%$ by volume; |
| 1,2-butadiene | $\leq 1\%$ by volume, preferably $\leq 0.5\%$ by volume, frequently from $\geq 0$ to 0.1% by volume; |
| 1-butyne | $\leq 0.5\%$ by volume, preferably $\leq 0.3\%$ by volume, frequently from 0 to 0.1% by volume; and |
| 2-butyne | $\leq 0.5\%$ by volume, preferably $\leq 0.3\%$ by volume, frequently from 0 to 0.1% by volume. |

Gas mixtures 2 which are suitable for the purposes of the present invention also include those which meet not only the abovementioned specifications but at the same time also meet the following specifications:

total other unsaturated $C_4$-hydrocarbons $\leq 0.5\%$ by volume, preferably $\leq 0.3\%$ by volume, frequently from 0 to 0.1% by volume;

total $C_5$-hydrocarbons $\leq 0.1\%$ by volume, usually $\leq 0.05\%$ by volume, generally from 0 to 300 ppm by volume;

total $C_6$–$C_8$-hydrocarbons $\leq 200$ ppm by volume, usually $\leq 150$ ppm by volume, generally from 0 to 30 ppm by volume;

acetone $\leq 100$ ppm by volume;

$C_1$–$C_4$-alcohols $\leq 100$ ppm by volume;

$C_2$–$C_4$-aldehydes $\leq 100$ ppm by volume;

acetylene $\leq 10$ ppm by volume;

total compounds containing carbonyl groups (calculated as $Ni(CO)_4$) $\leq 100$ ppm by volume;

ionogenic chlorine $\leq 1$ mg/kg, generally from 0 to 0.2 mg/kg;

total Cl-containing compounds, expressed as Cl, $\leq 1$ mg/kg, generally from 0 to 0.2 mg/kg;

total F-containing compounds, expressed as F, $\leq 1$ mg/kg, generally from 0 to 0.2 mg/kg; and total S-containing compounds, expressed as S, $\leq 10$ mg/kg, frequently from 0 to 1 mg/kg, generally from 0 to 0.1 mg/kg;

with the proviso that in all the abovementioned cases the total content of all butenes is preferably $\leq 1\%$ by volume (particularly preferably $\leq 0.75\%$ by volume and very particularly preferably $\leq 0.5\%$ by volume) and particularly preferably the total content of $C_4$-hydrocarbons is at the same time $\leq 3\%$ by volume (preferably $\leq 2\%$ by volume and particularly preferably $\leq 1\%$ by volume).

Unspecified compounds (constituents) are preferably not present, i.e. undetectable, in the gas mixtures 2 of the invention.

Such gas mixtures 2 are generally also obtainable in the process of the present invention, in particular if the separation processes mentioned are employed for converting gas mixtures 1 into gas mixtures 1' meeting the requirements specified according to the present invention, when the first step is carried out using crude propanes which contain $\geq 100$ ppm by weight, or $\geq 150$ ppm by weight, or $\geq 200$ ppm by weight of $C_4$-hydrocarbons or, for example, up to 6% by volume (e.g. from 0.1% by volume or 0.5% by volume to 6% by volume) of said $C_4$-hydrocarbons, in particular when they meet the following specification:

propane content ≧90% by volume, usually ≧93% by volume, generally ≧95% by volume;

content of propane and propylene ≦99.75% by volume or ≦99.5% by volume, usually ≦99% by volume or ≦98% by volume, generally ≦97% by volume;

total content of $C_4$-hydrocarbons ≦6% by volume, usually ≦5% by volume, generally ≦4% by volume; but frequently ≧0.5% by volume or ≧1% by volume, sometimes ≧2% by volume or even ≧3% by volume;

1-butene content ≦0.5% by volume, usually ≦0.3% by volume, generally ≦0.1% by volume; but frequently ≧5 ppm by volume, sometimes ≧10 ppm by volume or even ≧20 ppm by volume;

total content of butenes ≦0.5% by volume, usually ≦0.3% by volume, generally ≦0.1% by volume; but frequently ≧10 ppm by volume, sometimes ≧20 ppm by volume or even ≧30 ppm by volume;

ethane content ≦10% by volume, usually ≦5% by volume, generally from 0 to 2% by volume;

ethylene content ≦5% by volume, usually ≦2% by volume, generally from 0 to 0.5% by volume;

methane content ≦5% by volume, usually ≦2% by volume, generally from 0 to 0.2% by volume;

cyclopropane content ≦0.1% by volume;

propylene content ≦10% by volume, usually ≦5% by volume, generally ≦2% by volume;

total content $C_3$-hydrocarbons other than propane and propylene ≦0.3% by volume;

total content of $C_5$-hydrocarbons ≦0.3% by volume; and total content of $C_6$–$C_8$-hydrocarbons ≦600 ppm by volume.

Crude propanes suitable for the purposes of the present invention also include those which not only meet the above-mentioned specifications but also at the same time also meet the following specifications:

total content of oxygen-containing organic compounds ≦300 ppm by volume;

acetylene content ≦30 ppm by volume;

content of ionogenic chlorine ≦1 mg/kg;

total content of Cl-containing compounds, expressed as Cl, ≦1 mg/kg;

total content of F-containing compounds, expressed as F, ≦1 mg/kg;

total content of S-containing compounds, expressed as S, ≦10 mg/kg (in the case of catalytic dehydrogenations, it can be advantageous for the reaction gas mixture to contain, based on the propane present therein, from 1 to 1000 ppm by volume, preferably from 1 to 100 ppm by volume, of sulfur-containing compounds (e.g. $H_2S$ and/or dimethyl sulfide) since these are able, firstly, to passivate steel constituents (of the reactor) such as Ni, Cr and Fe (which reduces undesirable cracking of propane) and, secondly, to activate the catalysts used (cf. "Catalytic dehydrogenation of lower alkanes, Resasco, Daniel E.; Haller, Gary L., University Oklahoma, USA, Catalysis (1994), 11, 379–411");

with the proviso that the 1-butene content is preferably ≦0.1% by volume and particularly preferably the total content of butenes is at the same time ≦0.1% by volume and very particularly preferably the total content of $C_4$-hydrocarbons is at the same time ≦3% by volume or ≦2.5% by volume or ≦2% by volume.

The specifications for the crude propane defined under the proviso are in general suitable for the process of the present invention when the gas mixture 1 as such is, as a constituent of a gas mxiture 2, subjected to a heterogeneously catalyzed gas-phase partial oxidation and/or a partial gas-phase ammoxidation of the propylene present in the gas mixture 1. Here, the fact that a limited oxydehydrogenation and/or dehydrogenation conversion has an overall favorable effect according to the present invention in the first step of the process of the present invention is advantageous. In general this conversion is ≧5 mol %, but ≦30 mol, frequently ≦25 mol % and often ≦20 mol %, for each individual saturated hydrocarbon present.

The above-specified (but also all other) crude propanes suitable for the process of the present invention normally contain at least 0.25% by volume or at least 0.5% by volume or at least 1% by volume, frequently at least 1.5% by volume or at least 2% by volume and often at least 2.5% by volume or at least 3% by volume, of constituents other than propane and propylene (but frequently ≦10% by volume, usually ≦7% by volume and generally ≦5% by volume, of these constituents). These contents of extraneous substances usually also apply to other crude propanes suitable for the process of the present invention, e.g. those which are free of $C_4$-hydrocarbons. However, these can contain ≧0.1% by volume, or ≧0.5% by volume, frequently up to 6% by volume of $C_4$-hydrocarbons (e.g. from 0.1 or 0.5% by volume to 6% by volume). In addition and at the same time, they can contain ≧5 ppm by volume, frequently up to 0.5% by volume of butenes (e.g. from 5 ppm by volume to 0.5% by volume). Furthermore, they can also at the same time contain ≧5 ppm by volume, frequently up to 0.5% by volume of 1-butene (e.g. from 5 ppm by volume to 0.5% by volume).

Crude propanes which are particularly suitable for the purposes of the present invention also include those which meet not only the abovementioned specifications but at the same time also meet the following specifications:

Ag≦1 μg/kg;
Al≦10 μg/kg;
As≦1 μg/kg;
Au≦1 μg/kg;
Ba≦1 μg/kg;
Be≦1 μg/kg;
Bi≦1 μg/kg;
Ca≦2 μg/kg;
Cd≦1 μg/kg;
Co≦1 μg/kg;
Cr≦1 μg/kg;
Cu≦1 μg/kg;
Fe≦10 μg/kg;
Ga≦1 μg/kg;
Ge≦1 μg/kg;
Hg≦1 μg/kg;
In≦1 μg/kg;
Ir≦1 μg/kg;
K≦1 μg/kg;
Li≦1 μg/kg;
Mg≦1 μg/kg;
Mn≦1 μg/kg;
Mo≦1 μg/kg;
Na≦1 μg/kg;
Nb≦1 μg/kg;
Ni≦1 μg/kg;
Pb≦1 μg/kg;
Pd≦1 μg/kg;
Pt≦1 μg/kg;
Rh≦1 μg/kg;
Sb≦1 μg/kg;
Sn≦1 μg/kg;
Sr≦1 μg/kg;
Ta≦1 μg/kg;

Ti≦1 µg/kg;
Tl≦1 µg/kg;
V≦1 µg/kg;
Zn≦1 µg/kg; and
Zr≦1 µg/kg.

Crude propanes which are very particularly suitable for the purposes of the present invention are those which not only simultaneously meet the abovementioned specifications but also at the same time meet the following specifications:
density at 20° C.=500±2.0 kg/m³;
vapor pressure at 20° C.=7.6±0.2 bar;
water≦10 mg/kg;
evaporation residue≦2 mg/kg.

The specifications indicated are based on determinations by means of gas chromatography and by means of atomic absorption spectrometry. The evaporation residue is based on a gravimetric determination. It generally comprises high-boiling hydrocarbons (e.g. green oil).

Unspecified constituents are preferably not present, i.e. undetectable, in the crude propanes which are particularly suitable according to the invention.

The process of the present invention is of particular importance when it is employed in the recirculation mode.

In this case, the desired target product is separated off from the product gas mixture from the gas-phase partial oxidation and/or ammoxidation by a known separation process and at least the unreacted propane present in this product gas mixture, in general together with unreacted propylene present therein, is recirculated to the oxydehydrogenation and/or dehydrogenation step and/or to the gas-phase partial oxidation and/or ammoxidation. The propane and propylene are usually recirculated (recycled) in this way as constituents of the tailgas remaining after the target product has been separated off without this tailgas being subjected to intermediate treatment or, when an intermediate treatment is carried out (e.g. to separate off CO, $CO_2$, $H_2$ and/or $O_2$ present therein prior to recirculation), this intermediate treatment is carried out with only limited efficiency. For example, even when the crude propane used contains only small proportions of 1-butene, other butenes and/or other $C_4$-hydrocarbons (e.g. total content of $C_4$-hydrocarbons ≧0.01% by volume, possibly up to 6% by volume), these can accumulate in the gas mixture 2 when the gas recycle mode is employed and their concentrations can exceed the limits specified according to the present invention unless particular measures are undertaken. These measures can, for example, comprise selectively separating off the $C_4$-hydrocarbons by rectification and/or by absorption/desorption and/or stripping and/or by adsorption/desorption and/or by condensation and/or by membrane methods from the tailgas remaining after the target product has been separated off and only circulating the tailgas comprising propane and propylene which then remains.

EP-A 938463 regards such a separation step as unnecessary, although it recommends using the gas mixture 1 as such for the partial oxidation and using crude propane of essentially any purity for the first step.

As an alternative to the gas recycle mode, the tailgases mentioned can also be passed to other uses so as to avoid undesirable accumulation of $C_4$-hydrocarbons. For example, they together with the propane and propylene present therein can be burnt for generating electric power and/or be used for the production of synthesis gas and the like.

Otherwise, the process of the present invention can be carried out according to the different basic variants described in the prior art.

In the simplest variant, all steps of the process of the present invention are carried out in a single reaction zone and over a catalyst charge present therein, for example as taught in the documents EP-A 608838, EP-A 529853, DE-A 19835247, EP-A 895809, JP-A 7-232071, JP-A 11-169716, EP-A 1192987, JP-A 10-57813, JP-A 2000-37623, JP-A 10-36311, WO 00/29105, EP-A 767164, DE-A 10029338, JP-A 8-57319, JP-A 10-28862, JP-A 11-43314, JP-A 11-574719, WO 00/29106, JP-A 10-330343, JP-A 11-285637, JP-A 310539, JP-A 11-42434, JP-A 11-343261, JP-A 3423262, WO 99/03825, JP-A 7-53448, JP-A 2000-51693, JP-A 11-263745, DE-A 10046672, DE-A 10118814, DE-A 10119933, JP-A 2000/143,244, EP-A 318295, EP-A 603836, DE-A 19832033, DE-A 19836359, EP-A 962253, DE-A 10119933, DE-A 10051419, DE-A 10046672, DE-A 10033121, DE-A 101 459 58, DE-A 10122027, EP-A 1193240 and the references cited in these documents.

The active compositions to be used in the catalyst charge are essentially multimetal oxide compositions comprising the elements Mo, V, at least one of the two elements Te and Sb, and at least one element selected from the group consisting of Nb, Ta, W, Ti, Al, Zr, Cr, Mn, Ga, Fe, Ru, Co, Rh, Ni, Pd, Pt, La, Bi, B, Ce, Sn, Zn, Si, Na, Li, K, Mg, Ag, Au and In in combination.

The combination preferably comprises the elements Nb, Ta, W and/or Ti from the latter group of the elements, particularly preferably the element Nb.

The relevant active multimetal oxide compositions preferably comprise the abovementioned element combination in the stoichiometry I

$$Mo_1V_bM^1_cM^2_d \quad (I),$$

where
$M^1$=Te and/or Sb,
$M^2$=at least one element from the group consisting of Nb, Ta, W, Ti, Al, Zr, Cr, Mn, Ga, Fe, Ru, Co, Rh, Ni, Pd, Pt, La, Bi, Ce, Sn, Zn, Si, Na, Li, K, Mg, Ag, Au and In,
b=0.01 to 1,
c=>0 to 1, and
d=>0 to 1.

According to the present invention, preference is given to $M^1$=Te and $M^2$=Nb, Ta, W and/or Ti. $M^2$ is preferably Nb.

The stoichiometric coefficient b is advantageously from 0.1 to 0.6. Correspondingly, the preferred range for the stoichiometric coefficient c is from 0.01 to 1 or from 0.05 to 0.4 and advantageous values of d are from 0.01 to 1 or from 0.1 to 0.6.

It is particularly favorable according to the present invention if the stoichiometric coefficients b, c and d are simultaneously in the abovementioned preferred ranges.

What has been said above applies particularly when the elements other than oxygen present in the active composition of the catalyst charge are entirely one of the abovementioned element combinations.

These are then, in particular, the active multimetal oxide compositions of the formula II

$$Mo_1V_bM^1_cM^2_dO_n \quad (II),$$

where the variables have the meanings given for the formula I and n is a number which is determined by the valence and frequency of the elements other than oxygen in (II).

Furthermore, when the process of the present invention is carried out in the single-zone mode, preference is given to using active multimetal oxide compositions which firstly either comprise one of the abovementioned element combinations or, in terms of the elements other than oxygen, consist of it and at the same time have an X-ray diffraction pattern which displays reflections h and i whose maxima are at the diffraction angles (2Θ) 22.2±0.5° (h) and 27.3±0.5° (i) (all figures in this document relating to an X-ray diffraction pattern are based on an X-ray diffraction pattern produced using Cu—Kα radiation as X-radiation (Siemens diffractometer Theta-Theta D-5000, tube voltage: 40 kV, tube current: 40 mA, aperture diaphragm V20 (variable), scattered radiation diaphragm V20 (variable), secondary monochromator diaphragm (0.1 mm), detector diaphragm (0.6 mm), measuring interval (2Θ): 0.02°, measurement time per step: 2.4 s, detector: scintillation counter)).

The width at half height of these reflections can be very small or very pronounced.

For the purposes of the process of the present invention, particular preference is given to those among the abovementioned active multimetal oxide compositions whose X-ray diffraction pattern displays, in addition to the reflections h and i, a reflection k whose maximum is at 28.2±0.5° (k).

Among the latter, preference is in turn given, according to the present invention, to those whose reflection h is the most intense in the X-ray diffraction pattern and has a width at half height of not more than 0.5°, and very particular preference is given to those whose reflection i and reflection k each have a width at half height of ≦1° and have intensities $P_i$ and $P_k$, respectively, which obey the relationship 0.2≦R≦0.85, preferably 0.3≦R≦0.85, more preferably 0.4≦R≦0.85, particularly preferably 0.65≦R≦0.85, even more preferably 0.67≦R≦0.75 and very particularly preferably R=0.70 to 0.75 or R=0.72, where R is the intensity ratio defined by the formula $R=P_i/(P_i+P_k)$.

The abovementioned X-ray diffraction patterns preferably display no reflection whose maximum is at 2Θ=50±0.3°.

For the purposes of the present text, the definition of the intensity of a reflection in the X-ray diffraction pattern is the definition given in DE-A 19835247, DE-A 10122027, DE-A 10051419 and DE-A 10046672. The same applies to the definition of the width at half height.

Apart from the reflections h, i and k, the abovementioned X-ray diffraction patterns of active multimetal oxide compositions which can be used advantageously according to the present invention display further reflections whose maxima are at the following diffraction angles (2Θ):
9.0±0.4° (l)
6.7±0.4° (o) and
7.9±0.4° (p).

It is also advantageous for the X-ray diffraction pattern to display an additional reflection whose maximum is at a diffraction angle (2Θ) of 45.2±0.4° (q).

The X-ray diffraction pattern frequently also contains reflections at 29.2±0.4° (m) and 35.4±0.4°(n).

It is also advantageous for the element combinations defined in the formulae I and II to be present as a pure i phase. If the catalytically active oxide composition further comprises k phase, its X-ray diffraction pattern contains, in addition to the reflections mentioned above, further reflections whose maxima are at the following diffraction angles (2Θ): 36.2±0.4° and 50±0.4° (in the present text, the terms i phase and k phase are used as defined in DE-A 10122027 and DE-A 10119933).

If the reflection h is assigned an intensity of 100, it is advantageous for the purposes of the present invention for the reflections i, l, m, n, o, p, q to have the following intensities on the same intensity scale:

| | |
|---|---|
| i: | 5 to 95, frequently from 5 to 80, often from 10 to 60; |
| l: | 1 to 30; |
| m: | 1 to 40; |
| n: | 1 to 40; |
| o: | 1 to 30; |
| p: | 1 to 30 and |
| q: | 5 to 60. |

If the X-ray diffraction pattern displays reflections in addition to those mentioned above, the width at half height of these is generally ≦1°.

The specific surface area of the active multimetal oxide compositions of the formula II to be used according to the present invention or of active multimetal oxide compositions omprising element combinations of the formula I is frequently from 1 to 30 m²/g (BET surface area, nitrogen), especially when they have an X-ray diffraction pattern as described above.

The preparation of the active multimetal oxide compositions described is disclosed in the prior art cited in the context of them. Prior art references on this subject include, in particular, DE-A 10122027, DE-A 10119933, DE-A 10033121, EP-A 1192987, DE-A 10029338, JP-A 2000-143244, EP-A 962253, EP-A 895809, DE-A 19835247, WO 00/29105, WO 00/29106, EP-A 529853 and EP-A 608838 (in all examples in the latter two documents, spray drying is employed as drying method, e.g. at an inlet temperature of from 300 to 350° C. and an outlet temperature of from 100 to 150° C., countercurrent or cocurrent).

The active multimetal oxide compositions described can be used as such (i.e. in powder form) or after shaping to give suitable geometries (cf., for example, the coated catalysts of DE-A 10051419 and the geometric variants in DE-A 10122027) for the single-zone embodiment of the process of the present invention. They are particularly useful for preparing acrolein and/or acrylic acid and for preparing acrylonitrile.

The single-zone variant is based on the catalysts to be used being able to catalyze all steps of the process of the present invention.

It can be carried out either in a fixed catalyst bed or in a fluidized bed or moving bed of catalyst. Corresponding process descriptions may be found in the documents of the prior art. If the process of the present invention is carried out as a fixed-bed reaction, e.g. for preparing acrylic acid in the single-zone mode of operation, it is advantageously carried out in a shell-and-tube reactor whose tubes are charged with the catalyst. A liquid, generally a salt melt, is normally passed as heat transfer medium around the catalyst tubes. As an alternative, a thermoplate reactor in which the catalyst charge is present as a flat arrangement between cooling plates can also be used.

The reaction gas mixture is passed through the catalyst tubes in the reactor either in cocurrent or in countercurrent to the salt bath. The salt bath itself can have purely parallel flow relative to the catalyst tubes. However, a transverse flow can of course be superimposed on this. Overall, the salt bath can flow in a meandering manner around the catalyst tubes, with the flow being in cocurrent or in countercurrent to the reaction gas mixture only when viewed over the reactor. Shell-and-tube reactors suitable for the process of the present invention are disclosed, for example, in EP-A 700714 and EP-A 700893.

The various possible compositions of the reaction gas starting mixture for the single-zone variant of the process of the present invention can be taken from the prior art cited in connection with this process variant.

For the preparation of acrylic acid, the composition of the reaction gas starting mixture is typically within the following range (molar ratios):
Propane:oxygen:$H_2O$: other constituents (mainly inert diluent gases)=1:(0.1–10):($\geq$0–50):($\geq$0–50).

The abovementioned ratio is preferably 1:(0.5–5):(1–30):(1–30).

The abovementioned ranges apply particularly when the other constituents are predominantly molecular nitrogen. The reaction temperature is typically from 250 to 550° C. (the conditions for the ammoxidation are comparable, if the additional ammonia content of the reaction gas mixture is disregarded (cf., for example, EP-A 929853).

The space velocity of propane over a fixed-bed catalyst charge in the single-zone variant of the process of the invention can be, for example, from 10 to 500 standard l/l (fixed bed)·h. The space velocity of reaction gas starting mixture is frequently in the range from 100 to 10 000 standard l/l·h, often in the range from 500 to 5000 standard l/l·h.

The target product, e.g. acrylic acid, can be separated off from the resulting product gas mixture in a manner known per se, for example as described in DE-A 10122027, i.e. the acrylic acid present in the product gas mixture can, for example, be separated off by absorption in a high-boiling inert hydrophobic organic solvent (e.g. a mixture of diphenyl ether and biphenyl, which may further comprise additives such as dimethyl phthalate). The resulting mixture of absorbent and acrylic acid can subsequently be worked up in a manner known per se by rectification, extraction and/or crystallization to give pure acrylic acid. Alternatively, the initial separation of the acrylic acid from the product gas mixture can be carried out by fractional condensation as described, for example, in DE-A 10053086, DE-A 19627847, DE-A 19740253, DE-A 19740252, DE-A 19606877 and DE-A 19740253. The resulting acrylic acid condensate can then be purified further, for example by fractional crystallization (e.g. suspension crystallization and/or layer crystallization).

The tailgas mixture remaining after the initial separation of the acrylic acid comprises, in particular, unreacted propane and possibly unreacted propylene.

Depending on the 1-butene content, the total content of butenes and the total content of $C_4$-hydrocarbons of this tailgas mixture and the oxygen source used (whether pure oxygen, an oxygen-containing inert gas or air), the tailgas mixture can be recirculated as such. It is also possible to divide it into two parts of identical composition and to recirculate only one part and purge the other part (e.g. to pass it to incineration or another use (e.g. the production of synthesis gas)). The latter could of course also be done with the total amount of the tailgas mixture.

If relatively high proportions of the $C_4$ components which are undesirable according to the present invention and/or relatively high proportions of other undesirable components are present in the tailgas mixture, the propane and any propene present in the tailgas mixture can be separated off, e.g. by fractional pressure rectification (the separation factor can be selected appropriately), and subsequently recirculated to the process of the present invention and combined with the crude propane and other constituents of the reaction gas starting mixture. However, it may, for the purposes of the present invention, be sufficient to bring the tailgas into contact with a hydrophobic organic solvent which preferentially absorbs $C_3$-hydrocarbons in an extraction apparatus (e.g. by passing it through the organic solvent). The absorbed propane and possibly propene can subsequently be liberated again by desorption and/or stripping with air (which would in any case be required as oxygen source) and recirculated to the process of the present invention. Of course, the acrylic acid could also be separated off from the product mixture using the method described in DE-A 10059122. The active multimetal oxide compositions recommended for the single-zone variant can of course also be diluted with finely divided, e.g. colloidal, materials such as silicon dioxide, titanium dioxide, aluminum oxide, zirconium oxide and niobium oxide, for use in the process of the present invention.

The mass ratio of diluent to active composition can be up to 9 (diluent):1 (active composition), i.e. possible mass ratios are, for example, 6 (diluent):1 (active composition) and 3 (diluent):1 (active composition). The diluent can, as described in DE-A 10122027, be incorporated before or after the calcination. Of course, other catalyst systems as described, for example, in JP-A 3-170445, can also be used for the single-zone variant of the process of the present invention.

When the process of the present invention is actualized in one reaction zone, this amounts to one of the cases where gas mixture 1 and gas mixture 2 are identical. The process of the present invention is utilized here in particular when the limits specified according to the present invention for the levels of 1-butene and other C4-hydrocarbons in the product gas mixture of the process according to the present invention are exceeded.

According to the present invention, the process is preferably carried out in more than one reaction zone, as described, for example, in EP-A 938463, EP-A 117146, DE-A 3313573, GB-A 2118939, U.S. Pat. No. 3,161,670, WO 01/96270, EP-A 731077, DE-A 19837520, DE-A 19837517, DE-A 19837519, DE-A 19837518, DE-A 19837520, DE-A 10131297 and DE-A 10211275.

"More than one reaction zone" means first and foremost that at least one step of the process of the present invention is carried out under conditions which can, at least partly, be selected independently from those of the other step(s) within the process of the present invention or, but to only a secondary degree, that reaction conditions which are at least partly independent of one another are realized within one and the same step along the reaction path (the latter is the case when, for example, a multizone mode (with temperature zones which can be set independently of one another) is employed for one step, as described, for example, in DE-A 19948241, DE-A 19927624, DE-A 19910508, DE-A 19910506 and DE-A 19948248). Thus, if the process of the present invention comprises, for example, two steps, the catalyst or catalyst charge used in the first step could, for example, be different from that in the second step, or identical catalysts or catalyst charges could be used for both steps but the reaction temperatures in the two steps could be selected and adjusted independently of one another. Naturally, a combination of both can also be employed.

The advantage of the multizone variant is that it in principle makes it possible to achieve improved matching of the reaction conditions to the requirements of the individual steps of the process of the present invention.

This advantage is well known from the heterogeneously catalyzed gas-phase partial oxidation of propylene to acrylic acid using molecular oxygen.

It in principle proceeds in two successive steps along the reaction coordinate, with the first step leading to acrolein and the second leading from acrolein to acrylic acid.

This reaction variant produces, in a manner known per se, the opportunity of carrying out the partial oxidation according to the present invention of the propylene present in the gas mixture 2 in two oxidation zones arranged in series, with the oxidic catalyst used in each of the two oxidation zones being able to be optimized (this flexibility also allows the partial oxidation of the propylene to be stopped at acrolein and the acrolein to be isolated). In the first oxidation zone (propylene→acrolein), preference is generally given to a catalyst based on multimetal oxides comprising the element combination Mo—Bi—Fe, while catalysts based on multimetal oxides comprising the element combination Mo—V (e.g. those which have been recommended in this text for the single-zone variant) are normally preferred for the second oxidation zone (acrolein→acrylic acid). In principle, however, these two reaction steps can also be carried out in a single reaction zone and over a single catalyst.

In general, the first step will advantageously be carried out in a separate reaction zone in the process of the present invention.

In the case of an oxydehydrogenation of propane, this can be carried out as a homogeneous and/or heterogeneously catalyzed gas-phase oxydehydrogenation of propane to propylene using molecular oxygen. Air, pure molecular oxygen or air enriched with molecular oxygen can be used as source of molecular oxygen.

If the reaction zone is configured as a homogeneous oxydehydrogenation, this can in principle be carried out as described, for example, in U.S. Pat. No. 3,798,283, CN-A 1 105 352, Applied Catalysis, 70(2) 1991, pp. 175–187, Catalysis Today 13, 1992, pp. 673–678, and in DE-A 19 622 331. An advantageous oxygen source is air. The temperature of the homogeneous oxydehydrogenation is advantageously chosen within the range from 300 to 700° C., preferably from 400 to 600° C., particularly preferably from 400 to 500° C. The working pressure can be from 0.5 to 100 bar, in particular from 1 to 10 bar. The residence time is usually from 0.1 or 0.5 to 20 seconds, preferably from 0.1 or 0.5 to 5 seconds.

As reactor, it is possible to use, for example, a tube furnace or a shell-and-tube reactor, for example a countercurrent tube furnace using a flue gas as heat transfer medium or a shell-and-tube reactor using a salt melt as heat transfer medium. The propane to oxygen ratio in the starting mixture is preferably from 0.5:1 to 40:1, in particular from 1:1 to 6:1, more preferably from 2:1 to 5:1. The starting mixture can further comprise other, preferably inert, constituents (for the purposes of the present text, inert constituents are preferably constituents which react to an extent of less than 5 mol %, preferably less than 3 mol % and particularly preferably less than 1 mol %; they very particularly preferably do not react at all), for example water, carbon dioxide, carbon monoxide, nitrogen, noble gases, other hydrocarbons (e.g. secondary constituents present in the crude propane) and/or propylene, etc. Such constituents can also include constituents of the recirculated gas.

If the propane dehydrogenation is a heterogeneously catalyzed oxydehydrogenation, it can in principle be carried out as described, for example, in U.S. Pat. No. 4,788,371, CN-A 1073893, Catalysis Letters 23 (1994), 103–106, W. Zhang, Gaodeng Xuexiao Huaxue Xuebao, 14 (1993), 566, Z. Huang, Shiyou Huagong, 21 (1992) 592, WO 97/36849, DE-A 197 53 817, U.S. Pat. No. 3,862,256, U.S. Pat. No. 3,887,631, DE-A 195 30 454, U.S. Pat. No. 4,341,664, J. of Catalysis 167, 560–569 (1997), J. of Catalysis 167, 550–559 (1997), Topics in Catalysis 3 (1996) 265–275, U.S. Pat. No. 5,086,032, Catalysis Letters 10 (1991), 181–192, Ind. Eng. Chem. Res. 1996, 35, 14–18, U.S. Pat. No. 4,255,284, Applied Catalysis A: General, 100 (1993), 111–130, J. of Catalysis 148, 56–67 (1994), V. Cortés Corberán and S. Vic Bellón (Ed.), New Developments in Selective Oxidation II, 1994, Elsevier Science B. V., pp. 305–313, 3$^{rd}$ World Congress on Oxidation Catalysis, R. K. Grassellij S. T. Oyama, A. M. Gaffney and J. E. Lyons (Ed.), 1997, Elsevier Science B. V., p. 375 ff, or DE-A 19837520, DE-A 19837517, DE-A 19837519 and DE-A 19837518. Air can also be used as oxygen source in this case. However, the oxygen source here frequently comprises at least 90 mol % of molecular oxygen and often at least 95 mol % of oxygen.

The catalysts suitable for the heterogeneously catalyzed oxydehydrogenation are subject to no particular restriction. All oxydehydrogenation catalysts which are known to those skilled in the art and are able to oxidize propane to propylene are suitable. In particular, it is possible to use all oxydehydrogenation catalysts mentioned in the documents cited above. Suitable catalysts include, for example, oxydehydrogenation catalysts comprising MoVNb oxides or vanadyl pyrophosphate, if appropriate together with a promoter. One example of a useful oxydehydrogenation catalyst is a catalyst as has also been recommended for the single-zone variant, which comprises a mixed metal oxide with Mo, V, Te, O and X as significant constituents, where X is at least one element selected from among niobium, tantalum, tungsten, titanium, aluminum, zirconium, chromium, manganese, gallium, iron, ruthenium, cobalt, rhodium, nickel, palladium, platinum, antimony, bismuth, boron, indium, silicon, lanthanum, sodium, lithium, potassium, magnesium, silver, gold and cerium (cf. EP-A 938463 and EP-A 167109). Further particularly useful oxydehydrogenation catalysts are the multimetal oxide compositions or catalysts A of DE-A-197 53 817 and the catalysts of DE-A 19838312, with the multimetal oxide compositions or catalysts A mentioned as preferred in the first document being especially advantageous. This means that especially useful active compositions are multimetal oxide compositions of the formula III

$$M^1{}_a Mo_{1-b} M^2{}_b O_x \tag{III}$$

where
  $M^1$=Co, Ni, Mg, Zn, Mn and/or Cu,
  $M^2$=W, V, Te, Nb, P, Cr, Fe, Sb, Ce, Sn and/or La,
  a=0.5–1.5,
  b=0–0.5 and
  x=a number which is determined by the valence and abundance of elements other than oxygen in (III).

In principle, suitable active compositions (III) can be prepared in a simple manner by producing a very intimate, preferably finely divided, dry mix having a composition corresponding to their stoichiometry from suitable sources of their elemental constituents and calcining this at from 450 to 1000° C. Possible sources of the elemental constituents of the active multimetal oxide compositions (III) are oxides and/or compounds which can be converted into oxides by heating, at least in the presence of oxygen. Such compounds include, in particular, halides, nitrates, formates, oxalates, citrates, acetates, carbonates, ammine complex salts, ammonium salts and/or hydroxides. The intimate mixing of the starting compounds for preparing the multimetal oxide compositions (III) can be carried out dry, for example as finely divided powders, or wet, for example using water as liquid medium. The multimetal oxide compositions (III) can be used either in powder form or after shaping to particular catalyst geometries; in the latter case, shaping can be carried out before or after the final calcination. It is possible to use all-active catalysts, but the shaping of a pulverulent active composition or precursor composition can also be carried out by applying it to preshaped inert catalyst supports. As support materials, it is possible to use customary, porous or nonporous aluminum oxides, silicon dioxide, thorium dioxide, zirconium dioxide, silicon carbide or silicates, with the support bodies being able to have a regular or irregular shape.

In the heterogeneously catalyzed oxydehydrogenation of propane, the reaction temperature is preferably in the range from 200 to 600° C., in particular from 250 to 500° C., more preferably from 350 to 440° C. The working pressure is preferably in the range from 0.5 to 10 bar, in particular from 1 to 10 bar, more preferably from 1 to 5 bar. Working pressures above 1 bar, for example from 1.5 to 10 bar, have been found to be particularly advantageous. The heterogeneously catalyzed oxydehydrogenation of propane is generally carried out over a fixed bed of catalyst. The latter is advantageously installed in the tubes of a shell-and-tube reactor, as described, for example, in EP-A-0 700 893 and EP-A-0 700 714 and the references cited in these documents. The mean residence time of the reaction gas mixture in the catalyst bed is advantageously from 0.5 to 20 seconds. The ratio of propane to oxygen varies with the desired conversion and the selectivity of the catalyst, but is advantageously in the range from 0.5:1 to 40:1, in particular from 1:1 to 6:1, more preferably from 2:1 to 5:1. In general, the propylene selectivity decreases with increasing propane conversion. For this reason, the propane-to-propylene reaction is preferably carried out so that relatively low conversions of propane at high selectivities to propylene are achieved. The conversion of propane is particularly preferably in the range from 5 to 40 mol %, frequently in the range from 10 to 30 mol %. Here the term "propane conversion" means the proportion of the propane fed in (sum of the propane present in the crude propane and that present in any recirculated gas) which is reacted in a single pass. In general, the selectivity of propylene formation is from 50 to 98 mol %, more preferably from 80 to 98 mol %, with the term "selectivity" referring to the number of moles of propylene which are produced per 1 mol of propane reacted, expressed as a molar percentage.

In general, the starting mixture used in the oxidative dehydrogenation of propane contains from 5 to 95 mol % of propane (based on 100 mol % of starting mixture). Apart from propane and oxygen, the starting mixture for the heterogeneously catalyzed oxydehydrogenation can further comprise other, in particular inert, constituents such as carbon dioxide, carbon monoxide, nitrogen, nobel gases, other hydrocarbons, e.g. secondary constituents present in the crude propane, and/or propylene. The heterogeneous oxydehydrogenation can also be carried out in the presence of diluents such as steam.

Any reactor sequence known to those skilled in the art can be used for carrying out the homogeneous oxydehydrogenation or the heterogeneously catalyzed oxydehydrogenation of propane. For example, the oxydehydrogenation can be carried out in a single reactor or in a cascade of two or more reactors, between which oxygen may, if desired, be introduced. It is also possible to combine the homogeneous oxydehydrogenation and the heterogeneously catalyzed oxydehydrogenation with one another.

As possible constituents, the product mixture from a propane oxydehydrogenation according to the present invention can comprise, for example, the following components: propylene, propane, carbon dioxide, carbon monoxide, water, nitrogen, oxygen, ethane, ethene, methane, acrolein, acrylic acid, ethylene oxide, butane (e.g. n-butane or isobutane), acetic acid, formaldehyde, formic acid, propylene oxide and butenes (e.g. 1-butene). A product mixture obtained in the propane oxydehydrogenation of the invention typically comprises: from 5 to 10 mol % of propylene, from 0.1 to 2 mol % of carbon monoxide, from 1 to 3 mol % of carbon dioxide, from 4 to 10 mol % of water, from 0 to 1 mol % of nitrogen, from 0.1 to 0.5 mol % of acrolein, from 0 to 1 mol % of acrylic acid, from 0.05 to 0.2 mol % of acetic acid, from 0.01 to 0.05 mol % of formaldehyde, from 1 to 5 mol % of oxygen, from 0.1 to 1.0 mol % of further abovementioned components and, as balance, mostly propane, in each case based on 100 mol % of product mixture.

In general, the propane dehydrogenation in the first reaction zone can also be carried out as a heterogeneously catalyzed propane dehydrogenation with substantial exclusion of oxygen, as described in DE-A 3313573, WO 01/96270, DE-A 10131297 or DE-A 10211275 or as follows.

Since the heterogeneously catalyzed dehydrogenation reaction occurs with an increase in volume, the conversion can be increased by reducing the partial pressure of the products. This can be achieved in a simple manner, for example by carrying out the dehydrogenation under reduced pressure and/or by mixing in essentially inert diluent gases, e.g. steam which is normally an inert gas with respect to the dehydrogenation reaction. Dilution ith steam generally gives the further advantage of reduced carbonization of the catalyst used, since water vapor reacts with the carbon formed according to the principle of coal gasification. Steam can also be used as diluent gas in the subsequent oxidation and/or ammoxidation zone or zones (in the present text also referred to as partial zone or zones for short). Water vapor (steam) can also be separated off partly or completely from the product mixture from the dehydrogenation in a simple manner, for example by condensation, which opens up the opportunity of increasing the proportion of diluent gas $N_2$ when the modified product mixture obtainable in this way is employed further in the partial zone or zones. Further suitable diluents for the heterogeneously catalyzed dehydrogenation of propane are, for example, CO, methane, ethane, $CO_2$, nitrogen and noble gases such as He, Ne and Ar. All diluents mentioned can be used either on their own or in the form of various mixtures. It is advantageous for the diluents mentioned generally also being suitable diluents in the partial zone or zones. As already mentioned, preference is given to diluents which are inert (i.e. undergo chemical changes to an extent of less than 5 mol %, preferably less than 3 mol % and more preferably less than 1 mol %) in the respective reaction zone. In principle, all dehydrogenation catalysts known from the prior art are suitable for the heterogeneously catalyzed dehydrogenation of propane. They can be roughly divided into two groups, namely those which are oxidic in nature (for example chromium oxide and/or aluminum oxide) and those which comprise at least one, generally comparatively noble, metal (for example platinum) on a generally oxidic support.

It is thus possible to use, inter alia, all dehydrogenation catalysts recommended in WO 01/96270, EP-A 731077, DE-A 10211275, DE-A 10131297, WO 99/46039, U.S. Pat. No. 4,788,371, EP-A-0 705 136, WO 99/29420, U.S. Pat. Nos. 4,220,091, 5,430,220, 5,877,369, EP-A-0 117 146, DE-A 199 37 196, DE-A 199 37 105 and DE-A 199 37 107. In particular, the catalysts described in Example 1, Example 2, Example 3 and Example 4 of DE-A 199 37 107 can be used.

These are dehydrogenation catalysts comprising from 10 to 99.9% by weight of zirconium dioxide, from 0 to 60% by weight of aluminum oxide, silicon dioxide and/or titanium dioxide and from 0.1 to 10% by weight of at least one element of main group I or II, an element of transition group III, an element of transition group VIII of the Periodic Table of the Elements, lanthanum and/or tin, with the proviso that the sum of the percentages by weight is 100% by weight.

To carry out the heterogeneously catalyzed dehydrogenation of propane, all types of reactor and process variants known from the prior art are possible in principle. Descriptions of such process variants are given in, for example, all documents of the prior art cited in respect of dehydrogenation catalysts.

A comparatively comprehensive description of dehydrogenation processes suitable for the purposes of the present invention is also given in "Catalytica® Studies Division, Oxidative Dehydrogenation and Alternative Dehydrogenation Processes", Study Number 41920D, 1993, 430 Ferguson Drive, Mountain View, Calif., 94043-5272 U.S.A.

A characteristic of the partial heterogeneously catalyzed dehydrogenation of propane is that it proceeds endothermically. This means that the heat (energy) necessary for setting the required reaction temperature has to be introduced into the reaction gas starting mixture before and/or during the heterogeneously catalyzed dehydrogenation.

Furthermore, owing to the high reaction temperatures required, heterogeneously catalyzed dehydrogenations of propane typically suffer from formation of small amounts of high-boiling high molecular organic compounds through to carbon which deposit on the catalyst surface and thus deactivate the catalyst. To minimize this disadvantageous phenomenon, the propane-containing reaction gas mixture which is to be passed over the catalyst surface at elevated temperature in the heterogeneously catalyzed dehydrogenation can be diluted with steam. Under the resulting conditions, carbon which has deposited is partly or completely eliminated by the principle of coal gasification.

Another possible way of eliminating carbon compounds which have been deposited is to pass an oxygen-containing gas through the dehydrogenation catalyst at elevated temperature from time to time and thus effectively burn off the carbon which has been deposited. However, substantial suppression of the formation of carbon deposits can also be achieved by adding molecular hydrogen to the propane which is to be dehydrogenated over a heterogeneous catalyst before it is passed at elevated temperature over the dehydrogenation catalyst.

Of course, it is also possible to add a mixture of steam and molecular hydrogen to the propane which is to be dehydrogenated in the presence of a heterogeneous catalyst. Addition of molecular hydrogen to the heterogeneously catalyzed dehydrogenation of propane also reduces the undesirable formation of allene (propadiene), propyne and acetylene as by-products.

A suitable form of reactor for the heterogeneously catalyzed dehydrogenation of propane is a fixed-bed tube reactor or shell-and-tube reactor, i.e. the dehydrogenation catalyst is present as a fixed bed in a reaction tube or a bundle of reaction tubes. The reaction tubes are heated by a gas, for example a hydrocarbon such as methane, being burnt in the space surrounding the reaction tubes. It is advantageous to employ this direct form of heating of the catalyst tubes only in the first about 20–30% of the fixed bed and to heat the remaining length of the bed to the required reaction temperature by means of the radiant heat liberated in the combustion process. In this way, approximately isothermal reaction conditions can be achieved. Suitable internal diameters of the reaction tubes are from about 10 to 15 cm. A typical shell-and-tube dehydrogenation reactor has from 300 to 1000 reaction tubes. The temperature in the interior of the reaction tubes ranges from 300 to 700° C., preferably from 400 to 700° C. The reaction gas starting mixture is advantageously preheated to the reaction temperature before it is fed into the tube reactor. It is possible for the product gas mixture to leave the reaction tube at a temperature which is from 50 to 100° C. lower. However, this outlet temperature can also be higher or the same. In the abovementioned procedure, the use of oxidic dehydrogenation catalysts based on chromium oxide and/or aluminum oxide is advantageous. It is frequently advantageous to use no diluent gas but to start out from essentially only crude propane as starting reaction gas. The dehydrogenation catalyst, too, is usually employed in undiluted form.

On a large industrial scale, a plurality (e.g. three) of such shell-and-tube reactors can be operated in parallel. According to the present invention, it is possible for two of these reactors to be in dehydrogenation operation while the catalyst bed in a third reactor is being regenerated without production in the partial zone or zones being interrupted.

Such a procedure is advantageous in, for example, the BASF-Linde propane dehydrogenation process known from the literature. However, it is important according to the present invention that the use of such a shell-and-tube reactor is sufficient.

Such a procedure-can also be employed in the "steam active reforming (STAR) process" which has been developed by Phillips Petroleum Co. (cf., for example, U.S. Pat. Nos. 4,902,849, 4,996,387 and 5,389,342). As dehydrogenation catalyst in the STAR process, it is advantageous to employ promoter-containing platinum on zinc (magnesium) spinel as support (cf., for example, U.S. Pat. No. 5,073,662). As a difference from the BASF-Linde propane dehydrogenation process, the propane to be dehydrogenated is diluted with steam in the STAR process. A molar ratio of steam to propane in the range from 4 to 6 is typical. The reactor outlet pressure is frequently from 3 to 8 atm and the reaction temperature is advantageously from 480 to 620° C. Typical space velocities of the total reaction gas mixture over the catalyst are from 0.5 to 10 $h^{-1}$ (LHSV).

The heterogeneously catalyzed dehydrogenation of propane can also be carried out using a moving bed. For example, the moving catalyst bed can be accommodated in a radial flow reactor. In this, the catalyst slowly moves from the top downward while the reaction gas mixture flows radially. This mode of operation is employed, for example, in the UOP-Oleflex dehydrogenation process. Since the reactors are operated pseudoadiabatically in this process, it is advantageous to employ a plurality of reactors connected in series as a cascade (typically up to four reactors). In this way, excessively high differences between the temperature of the reaction gas mixture at the reactor inlet and the temperature at the reactor outlet can be avoided (in adiabatic operation, the reaction gas starting mixture functions as heat transfer medium on whose heat content the drop in the reaction temperature depends) while still achieving attractive total conversions.

When the catalyst bed has left the moving-bed reactor, it is passed to regeneration and subsequently reused. In this process, the dehydrogenation catalyst used can be, for example, a spherical dehydrogenation catalyst consisting essentially of platinum on a spherical aluminum oxide support. In the UOP variant, hydrogen is added to the propane to be dehydrogenated in order to avoid premature catalyst aging. The working pressure is typically from 2 to 5 atm. The hydrogen to propane molar ratio is advantageously from 0.1 to 1. The reaction temperatures are preferably from 550 to 650° C. and the space velocity of the reaction gas mixture over the catalyst is from about 2 to 6 $h^{-1}$.

In the fixed-bed process described, the catalyst geometry can likewise be spherical, but can also be cylindrical (hollow or solid) or be of some other shape.

As a further process variant for the heterogeneously catalyzed dehydrogenation of propane, Proceedings De Witt, Petrochem. Review, Houston, Tex., 1992 a, N1, describes the possibility of a heterogeneously catalyzed dehydrogenation of propane in a fluidized bed, in which the propane is not diluted.

According to the invention, it is possible, for example, for two fluidized beds to be operated side by side so that one can periodically be undergoing regeneration without adverse effects on the overall process. As active composition, use is made of chromium oxide on aluminum oxide. The working pressure is typically from 1 to 2 atm and the dehydrogenation temperature is generally from 550 to 600° C. The heat required for the dehydrogenation is introduced into the reaction system by preheating the dehydrogenation catalyst to the reaction temperature. The abovementioned way of carrying out the dehydrogenation is also known in the literature as the Snamprogetti-Yarsintex process.

As an alternative to the above-described procedures, the heterogeneously catalyzed dehydrogenation of propane with substantial exclusion of oxygen can also be carried out using a process developed by ABB Lummus Crest (cf. Proceedings De Witt, Petrochem. Review, Houston, Tex., 1992, P1).

The previously described heterogeneously catalyzed processes for the dehydrogenation of propane with substantial exclusion of oxygen are all operated at propane conversions of ≧30 mol % (generally ≦60 mol %) (based on a single pass through the reaction zone). An advantage of the present invention is that it is sufficient to achieve a propane conversion of from ≧5 mol % to ≧30 mol % or ≦25 mol %. This means that the heterogeneously catalyzed dehydrogenation of propane can also be carried out at propane conversions of from 10 to 20 mol % (the conversions are based on a single pass through the reaction zone). This is due, inter alia, to the remaining amount of unreacted propane functioning essentially as inert diluent gas in the subsequent partial zone or zones and later being able to be recirculated, essentially without losses, to the dehydrogenation zone and/or the partial zone or zones.

To realize the abovementioned propane conversions, it is advantageous to carry out the heterogeneously catalyzed dehydrogenation of propane at a working pressure of from 0.3 to 3 atm. It is also advantageous to dilute the propane which is to be dehydrogenated in the presence of a heterogeneous catalyst with steam. In this case, the heat capacity of the water partly compensates the effect of the endothermic nature of the dehydrogenation and the dilution with steam reduces the partial pressures of starting material and product, which has a favorable effect on the position of the equilibrium of the dehydrogenation. Furthermore, the use of steam has, as already mentioned, a favorable effect on the operating life of dehydrogenation catalysts comprising noble metals. If required, molecular hydrogen can also be added as a further constituent. The molar ratio of molecular hydrogen to propane is generally ≦5. The molar ratio of steam to propane can accordingly be, with a comparatively low propane conversion, from ≧0 to 30, advantageously from 0.1 to 2 and preferably from 0.5 to 1. Further advantageous found for a mode of operation with a low propane conversion are that only a comparatively small quantity of heat is consumed on a single pass of the reaction gas through the reactor and that comparatively low reaction temperatures are sufficient to achieve the conversion on a single pass through the reactor.

It can therefore be advantageous for the propane dehydrogenation at a comparatively low propane conversion to be carried out (pseudo)adiabatically. This means that the reaction gas starting mixture is generally heated initially to from 500 to 700° C. (or from 550 to 650° C.) (for example by direct firing around the wall surrounding it). A single adiabatic pass through a catalyst bed will then normally be sufficient to achieve the desired conversion, with the reaction gas mixture being cooled by about 30° C. to 200° C. (depending on conversion and dilution). Presence of steam as heat transfer medium also has an advantageous effect from the point of view of an adiabatic mode of operation. The lower reaction temperature makes longer operation lives of the catalyst bed used possible.

In principle, the heterogeneously catalyzed dehydrogenation of propane at a comparatively low propane conversion can be carried out in a fixed-bed reactor or in a moving-bed or fluidized-bed reactor, regardless of whether it is operated adiabatically or isothermally.

A noteworthy aspect of the process of the present invention is that a single shaft furnace reactor as fixed-bed reactor through which the reaction gas mixture flows axially and/or radially is sufficient for carrying it out, in particular in adiabatic operation.

In the simplest case, this is a single closed reaction volume, for example a vessel, whose internal diameter is from 0.1 to 10 m, possibly from 0.5 to 5 m, and in which the fixed catalyst bed is installed on a support device (for example a grating). The hot propane-containing reaction gas in this case flows axially through the reaction volume which is charged with catalyst and is thermally insulated in adiabatic operation. The catalyst geometry can be either spherical or annular or in the form of extrudates. Since in this case the reaction volume can be realized by means of a very inexpensive apparatus, all catalyst geometries which produce a particularly low pressure drop are preferred. These are, in particular, catalyst geometries which lead to a large empty volume or are structured, for example monoliths or honeycombs. To achieve radial flow of the propane-containing reaction gas, the reactor can, for example, comprise two concentric mesh cylinders located within an outer cylindrical wall, with the catalyst bed being installed in the annular gap between them. In the case of adiabatic operation, the outer cylindrical wall would once again be thermally insulated as appropriate.

Suitable catalysts for a heterogeneously catalyzed dehydrogenation of propane with a comparatively low propane conversion on a single pass are, in particular, the catalysts disclosed in DE-A 199 37 107, especially all those disclosed by way of example.

After a prolonged period of operation, the above-mentioned catalysts can be regenerated in a simple manner by, for example, passing air initially diluted with nitrogen and/or steam (preferred) in the first regeneration stages over the catalyst bed at an inlet temperature of from 300 to 600° C., frequently from 400 to 550° C. The space velocity of regeneration gas over the catalyst can, for example, be from 50 to 10000 $h^{-1}$ and the oxygen content of the regeneration gas can be from 0.5 to 20% by volume.

In the further regeneration stages which follow, air can be used as regeneration gas under otherwise identical regeneration conditions. It is advantageous in practice to flush the catalyst with inert gas (for example $N_2$) before regeneration.

Subsequently, it is generally advisable to regenerate the catalyst using pure molecular hydrogen or molecular hydrogen diluted with inert gas (preferably steam) (the hydrogen content should be $\geq 1\%$) under otherwise identical conditions.

The heterogeneously catalyzed dehydrogenation of propane at a comparatively low propane conversion ($\leq 30$ mol %) can in all cases be operated at the same space velocities (both of the total reaction gas and of the propane present in this) over the catalyst as in the variants with a high propane conversion (>30 mol %). This space velocity of reaction gas can be, for example, from 100 to 10000 $h^{-1}$, frequently from 300 to 5000 $h^{-1}$, i.e. often from about 500 to 3000 $h^{-1}$.

The heterogeneously catalyzed dehydrogenation of propane at a comparatively low propane conversion can be carried out particularly elegantly in a tray reactor.

This contains more than one catalyst bed catalyzing the dehydrogenation arranged physically separately in succession. The number of catalyst beds can be from 1 to 20, advantageously from 2 to 8 or from 3 to 6. The catalyst beds are advantageously arranged after one another in a radial or axial direction. It is advantageous in practice to employ a fixed-bed type of catalyst in such a tray reactor.

In the simplest case, the fixed catalyst beds are arranged axially in a shaft furnace reactor or in the annular gaps between concentric mesh cylinders. However, it is also possible to arrange the annular gaps in segments above one another and to pass the gas radially through one segment and into the next segment above or below it.

The reaction gas mixture is advantageously subject to intermediate heating in the tray reactor on its way from one catalyst bed to the next catalyst bed, for example by passing it over heat exchanger ribs heated by means of hot gases or by passing it through tubes heated by means of hot combustion gases.

If the tray reactor is operated adiabatically, it is sufficient to preheat the reaction gas mixture to from 450 to 550° C. before introducing it into the dehydrogenation reactor and keep it within this temperature range within the tray reactor in order to achieve the desired propane conversions ($\leq 30$ mol %), particularly when using the catalysts described in DE-A 199 37 107, in particular the embodiments described by way of example. Thus, the overall propane dehydrogenation can be carried out at extremely low temperatures, which is particularly advantageous in terms of the period of operation of the fixed catalyst beds between two regenerations.

An even more elegant approach is to carry out the catalytic dehydrogenation autothermally, that is, for example, to carry out the above-described intermediate heating in a direct fashion (autothermal operation). For this purpose, a limited amount of molecular oxygen is added to the reaction gas mixture either before it flows through the first catalyst bed and/or between the subsequent catalyst beds. Depending on the dehydrogenation catalyst used, this results in limited combustion of the hydrocarbons present in the reaction gas mixture, possibly carbon or carbon-like compounds which have been deposited on the catalyst surface and/or hydrogen formed during the course of the heterogeneously catalyzed dehydrogenation of propane and/or added to the reaction gas mixture (it can also be advantageous in practice to install catalyst beds provided with a catalyst which specifically (selectively) catalyzes the combustion of hydrogen (and/or hydrocarbon) in the tray reactor (examples of such catalysts are those described in U.S. Pat. Nos. 4,788,371, 4,886,928, 5,430,209, 5,530,171, 5,527,979 and 5,563,314; for example, such catalyst beds can be accommodated in the tray reactor in an alternating fashion between the beds containing the dehydrogenation catalyst)). The heat of reaction liberated thus makes possible, in a pseudoautothermal fashion, virtually isothermal operation of the heterogeneously catalyzed dehydrogenation of propane. In this way, when a longer residence time of the reaction gas in the catalyst bed is chosen, a propane dehydrogenation at a decreased or essentially constant temperature is possible, which makes it possible to achieve particularly long periods of operation between two regenerations.

In general, an introduction of oxygen of the type described above should be such that the oxygen content of the reaction gas mixture is from 0.5 to 30% by volume, based on the amount of propane and propylene present therein. As oxygen source, it is possible to use either pure molecular oxygen or oxygen diluted with inert gas, for example CO, $CO_2$, $N_2$, noble gases, in particular air. The resulting combustion gases generally have an additional diluting effect and in this way promote the heterogeneously catalyzed dehydrogenation of propane.

The heterogeneously catalyzed dehydrogenation of propane can be made more isothermal by installing closed internals (for example, tubular internals) which have advantageously but not necessarily been evacuated before being filled in the tray reactor in the spaces between the catalyst beds. Such internals can also be placed in the respective catalyst bed. These internals contain suitable solids or liquids which vaporize or melt above a particular temperature and in the process absorb heat and then recondense and release heat where the temperature is below this particular temperature.

One other possible way of heating the reaction gas starting mixture for the heterogeneously catalyzed dehydrogenation of propane to the required reaction temperature is to burn part of the propane and/or $H_2$ present therein by means of molecular oxygen (for example over specific combustion catalysts, e.g. by simply passing the reaction gas mixture over and/or through the catalyst) and heating the reaction gas mixture to the desired reaction temperature by means of the heat of combustion liberated in this way. The resulting combustion products such as $CO_2$, $H_2O$, and also any $N_2$ accompanying the molecular oxygen required for combustion advantageously constitute inert diluent gases.

The abovementioned hydrogen combustion can be achieved particularly elegantly in the manner described in DE-A 10211275, i.e. in a process for the continuous heterogeneously catalyzed partial dehydrogenation of propane in the gas phase, in which a reaction gas in which the propane to be dehydrogenated is present is fed continuously into a reaction zone, in the reaction zone, the reaction gas is passed over at least one fixed catalyst bed over which molecular hydrogen and to at least a partial extent propylene are formed by catalytic dehydrogenation, at least one gas comprising molecular oxygen is added to the reaction gas before and/or after entry into the reaction zone, in the reaction zone, the molecular oxygen partly oxidizes molecular hydrogen present in the reaction gas to form water vapor, and a product gas comprising molecular hydrogen, water vapor, propylene and propane is taken from the reaction zone, wherein the product gas taken from the reaction zone is divided into two parts having an identical composition and one of the two parts is recirculated as recycle gas to the dehydrogenation reaction zone and the other part is, according to the invention, used further as gas mixture 1.

This process variant is preferred particularly when recycle gas comprising propane and possibly propylene and originating from the partial zone or zones (which may, if desired, have been subjected to a removal of secondary components (e.g. $C_4$-hydrocarbons such as 1-butene)) is fed into the dehydrogenation zone as further propane source in addition to crude propane. This applies particularly when the recycle gas represents the sole oxygen source for the combustion of hydrogen in this process variant.

In the process of the present invention, the product gas mixture formed in the heterogeneously catalyzed dehydrogenation of propane generally comprises propane, propene, molecular hydrogen, $N_2$, $H_2O$, methane, ethane, ethylene, 1-butene, other butenes and other $C_4$-hydrocarbons (n-butane, isobutane, butadiene, etc.), CO and $CO_2$. It will generally be at a pressure of from 0.3 to 10 atm and frequently have a temperature of from 400 to 500° C., in favorable cases from 450 to 500° C.

While EP-A 117 146, DE-A 3 313 573 and U.S. Pat. No. 3,161,670 recommend using the product gas mixture formed in the heterogeneously catalyzed dehydrogenation or propane (gas mixture 1) as such as feed to the partial zone or zones, it is usually advantageous according to the present invention to separate off at least part of any $C_4$-hydrocarbons (e.g. 1-butene, n-butane, isobutane, other butenes, butadiene etc.) present in the product gas mixture (gas mixture 1) from the oxydehydrogenation and/or dehydrogenation before it is used further as feed to the partial zone or zones. If hydrogen is present in the gas mixture 1, the above-mentioned separation can be combined with at least partial separation of the hydrogen or such a hydrogen separation can be carried out beforehand.

The latter can, for example, be achieved by passing the gas mixture 1, if appropriate after it has been cooled in an indirect heat exchanger (the heat recovered is advantageously used for heating a feed gas required for the process of the present invention), over a generally tubular membrane which is permeable only to molecular hydrogen. The molecular hydrogen which has been separated off in this way can, if required, be partly returned to the heterogeneously catalyzed dehydrogenation of propane or passed to another use. For example, it can be burnt in fuel cells.

As an alternative, some or all of the hydrogen can be separated off by partial condensation, adsorption and/or rectification (preferably under superatmospheric pressure). The removal of part or all of the molecular hydrogen from the product gas mixture (gas mixture 1) in the process of the present invention can also be carried out by selective (e.g. heterogeneously catalyzed) combustion of the hydrogen by means of molecular oxygen. The water of reaction formed can either be separated off partly or completely or can be left in the gas mixture since it is able to function as inert diluent in the partial zone or zones. Catalysts suitable for this purpose are disclosed, for example, in U.S. Pat. Nos. 4,788, 371, 4,886,928, 5,430,209, 5 5,530,171, 5,527,979 and 5,563,314.

The selective combustion of molecular hydrogen can also be carried out effectively in situ during the heterogeneously catalyzed dehydrogenation, e.g. by oxidation over at least one reducible metal oxide added in addition to the dehydrogenation catalyst, as is described, for example, in EP-A 832056.

According to the present invention, it is advantageous to separate off at least 10 mol %, or at least 25 mol %, frequently at least 35 mol %, or at least 50 mol %, often at least 75 mol % or the total amount of the molecular hydrogen formed in the heterogeneously catalyzed dehydrogenation before and/or while the remaining product gas mixture (gas mixture 1') is used as feed to the partial zone or zones. If necessary, any water present in the gas mixture 1 can be separated off (e.g. by condensation) before the gas mixture is used further in the partial zone or zones. It goes without saying that other constituents of the product gas mixture (gas mixture 1) other than propane and propylene can also be separated off if required at the same time as molecular hydrogen and/or $C_4$-hydrocarbons such as 1-butene, etc., are separated off.

A simple possible way of achieving this is, for example, to bring the preferably cooled (preferably to from 10 to 70° C.) gas mixture 1, e.g. at a pressure of from 0.1 to 50 atm and a temperature of from 0 to 100° C., into contact with a (preferably high-boiling) organic solvent (preferably a hydrophobic solvent) in which propane and propene are preferentially absorbed (e.g. by simply passing the gas through the organic solvent). The propane and propene are recovered together in purified form by subsequent desorption, rectification and/or stripping with a gas which is inert in the partial zone or zones and/or is required as reactant in this reaction zone (e.g. air) and are used as feed to the partial zone or zones (as mentioned above, in the case of stripping with air, the gas mixture 1' generated in this way may be identical to the gas mixture 2, ie used as such directly as feed to the feed to the at least one partial oxidation. The offgas from the absorption, which may comprise molecular hydrogen, can, for example, be subjected to a membrane separation and, if required, the hydrogen which has been separated off can then be used in the heterogeneously catalyzed dehydrogenation of propane.

However, the $C_3$-hydrocarbons/$C_4$-hydrocarbons separation factor in the present separation process is comparatively limited and is frequently not sufficient to meet the requirements of the present invention.

As an alternative to the above-described separation step via absorption, preference is therefore frequently given to using a pressure swing adsorption or a pressure rectification for the purposes of the present invention.

Suitable absorption media for the above-described absorptive separation are in principle all absorption media which are able to absorb propane and propene. The absorption medium is preferably an organic solvent which is preferably hydrophobic and/or high-boiling. This solvent advantageously has a boiling point (at atmospheric pressure of 1 atm) of at least 120° C., preferably at least 180° C., more preferably from 200 to 350° C., in particular from 250 to 300° C., even more preferably from 260 to 290° C. The flash point (at atmospheric pressure of 1 atm) is advantageously above 110° C. In general, relatively nonpolar organic solvents, for example aliphatic hydrocarbons which preferably contain no externally acting polar group or else aromatic hydrocarbons, are generally suitable as absorption medium. In general, it is desirable that the absorption medium has a very high boiling point and at the same time a very high solvent capability for propane and propene. Examples of suitable absorption media are aliphatic hydrocarbons, for example $C_8$–$C_{20}$-alkanes or -alkenes, and aromatic hydrocarbons, for example middle oil fractions from paraffin distillation, and ethers having bulky groups on the O atom or mixtures thereof, with a polar solvent, such as the 1,2-dimethyl phthalate disclosed in DE-A 43 08 087, being able to be added to these. Further suitable absorption media are esters of benzoic acid and phthalic acid with straight-chain alkanols containing from 1 to 8 carbon atoms, e.g. n-butyl benzoate, methyl benzoate, ethyl benzoate, dimethyl phthalate, diethyl phthalate, and also heat transfer oils such as biphenyl, diphenyl ether and mixtures of biphenyl and diphenyl ether or their chlorinated derivatives and triarylalkenes, for example 4-methyl-4'-benzyldiphenylmethane and its isomers 2-methyl-2'-benzyldiphenylmethane, 2-methyl-4'-benzyldiphenylmethane and 4-methyl-2'-benzyldiphenylmethane and mixtures of such isomers. A suitable absorption medium is a solvent mixture of biphenyl and diphenyl ether, preferably one having the azeotropic composition, in particular a mixture consisting of about 25% by weight of biphenyl and about 75% by weight of diphenyl ether, for example the commercially available Diphyl® (e.g. purchased from Bayer Aktiengesellschaft). A solvent such as dimethyl phthalate is frequently added to this solvent mixture in an amount of from 0.1 to 25% by weight, based on the total solvent mixture. Further particularly useful absorption media are octanes, nonanes, decanes, undecanes, dodecanes, tridecanes, tetradecanes, pentadecanes, hexadecanes, heptadecanes and octadecanes, with tetradecanes having been found to be especially suitable. It is advantageous for the absorption medium used to meet the abovementioned boiling point requirement but at the same time have a molecular weight which is not too high. The molecular weight of the absorption medium is advantageously $\leqq 300$ g/mol. The paraffins having from 8 to 6 carbon atoms described in DE-A 33 13 573 are also suitable. Examples of suitable commercial products are products marketed by Haltermann, e.g. Halpasols i, such as Halpasol 250/340 i and Halpasol 250/275 i, and also printing ink oils sold under the names PKWF and Printosol. Preference is given to aromatic-free commercial products, e.g. those of the type PKWFaf.

The manner in which the absorption is carried out is not subject to any particular restrictions. It is possible to use all processes and conditions with which those skilled in the art are familiar. The gas mixture is preferably brought into contact with the absorption medium at a pressure of from 1 to 50 bar, preferably from 2 to 20 bar, more preferably from 5 to 10 bar, and a temperature of from 0 to 100° C., in particular from 30 to 50° C. The absorption can be carried out either in columns or in quench apparatuses. It can be carried out in cocurrent or in countercurrent. Examples of suitable absorption columns are tray columns (with bubble cap trays and/or sieve trays), columns having structured packing (e.g. sheet metal packing having a specific surface area of from 100 to 1000 $m^2/m^3$ or up to 750 $m^2/m^3$, for example Mellapak® 250 Y) and packed columns containing random packing (e.g. columns packed with Raschig rings). However, it is also possible to use trickle towers and spray towers, graphite block absorbers, surface absorbers such as thick-film and thin-film absorbers and also pan scrubbers, cross-spray scrubbers and rotary scrubbers. It can also be advantageous to allow absorption to take place in a bubble column with or without internals.

The propane and propene can be separated off from the absorption medium by stripping, flash evaporation and/or distillation.

The propane and propene are preferably separated off from the absorption medium by stripping and/or desorption. Desorption can be carried out in a customary manner by means of a pressure and/or temperature change, preferably at a pressure of from 0.1 to 10 bar, in particular from 1 to 5 bar, more preferably from 1 to 3 bar, and a temperature of from 0 to 200° C., in particular from 20 to 100° C., more preferably from 30 to 70° C., particularly preferably from 40 to 60° C. An example of a gas suitable for stripping is steam, but particular preference is given to oxygen/nitrogen mixtures, for example air. When air or an oxygen/nitrogen mixture having an oxygen content above 10% by volume is used, it can be advantageous to add a gas which reduces the explosive range before or during the stripping process. Particularly useful gases for this purpose are gases having a specific heat capacity of $\geqq 29$ J/mol·K at 20° C., for example methane, ethane, propane, propene, benzene, methanol, ethanol, and also ammonia, carbon dioxide and water. However, according to the present invention, $C_4$-hydrocarbons should be avoided as additives of this type. Bubble columns with or without internals are also particularly useful for stripping.

The propane and propene can also be separated off from the absorption medium by means of distillation or rectification, in which case it is possible to use customary columns containing ordered packing, random packing or appropriate internals. Preferred conditions in the distillation or rectification are a pressure of from 0.01 to 5 bar, in particular from 0.1 to 4 bar, more preferably from 1 to 3 bar, and a temperature (at the bottom) of from 50 to 300° C., in particular from 150 to 250° C.

A gas mixture 1' obtained by stripping from the absorption medium can be passed to a further process stage before it is used as feed to the partial zone or zones, for example to reduce the losses of costripped absorption medium (e.g. precipitation in demisters and/or deep bed filters) and thus at the same time protect the partial zone or zones from absorption medium or to achieve a further improvement in the separation of $C_3$-hydrocarbons from $C_4$-hydrocarbons. Such removal of the absorption medium can be carried out by all process steps known to those skilled in the art. An embodiment of such a separation which is preferred for the purposes of the process of the present invention is, for example, quenching of the starting stream from the stripping apparatus by means of water. In this case, the absorption medium is scrubbed from this laden starting stream by means of water and the starting stream is simultaneously loaded with water. This scrubbing or quenching can, for example, be carried out at the top of a desorption column over a liquid collection tray by countercurrent spraying with water or in a separate apparatus.

To aid the separation effect, internals which increase the quenching surface area, as are known to those skilled in the art from rectifications, absorptions and desorptions, can be installed in the quench region.

Water is a preferred scrubbing medium since it normally does not interfere in the subsequent partial zone or zones. After the water has scrubbed the absorption medium from the starting stream laden with propane and propene, the water/absorption medium mixture is passed to a phase separation and the treated starting stream is fed as gas mixture 1' to the partial zone.

Both the absorption medium which has been stripped free of $C_3$-hydrocarbons and the absorption medium recovered in the phase separation can be reused for the purposes of absorption.

The gas mixture 1 and/or the gas mixture 1' produced from the same can now be used in a manner known per se in at least one reaction zone for supplying a heterogeneously catalyzed gas-phase oxidation and/or ammoxidation of propene to acrolein and/or acrylic acid and/or acrylonitrile with a feed gas mixture 2. As oxidant, it is possible to add pure molecular oxygen, air, oxygen-enriched air or any other mixture of oxygen and inert gas. If the partial oxidation is the conversion of propylene into propylene oxide, the procedure described, for example, in EP-A 372972 can be employed.

If the oxidation reaction is a partial ammoxidation to acrylonitrile, it can be carried out, for example, as described in DE-A 2351151. In the case of a partial oxidation of propylene to acrolein and/or acrylic acid, the composition of the gas mixture 2 with concomitant use of the gas mixture 1 and/or 1' (it is also possible to use mixtures of the two, i.e. separation is carried out from one part but not from another) in the process of the present invention is set so that it is within the following molar ratio ranges:
Propane:propene:$N_2$:$O_2$:$H_2O$:others=0.5–20:1:0.1–40: 0.1–10:0–20:0–1.

According to the present invention, the abovementioned molar ratios are advantageously
2–10:1:0.5–20:0.5–5:0.01–10:0–1.

It is also advantageous, according to the present invention, for the abovementioned molar ratios to be
3–6:1:1–10:1–3:0.1–2:0–0.5.

As mentioned above, the heterogeneously catalyzed gas-phase partial oxidation of propylene to acrylic acid by means of molecular oxygen proceeds in two steps which follow one another along the reaction coordinate and of which the first leads to acrolein and the second from acrolein to acrylic acid.

This reaction sequence in two steps which follow one another in time makes it possible in a manner known per se for the partial zone or zones of the process of the present invention in this case to be in the form of two successive oxidation zones, so that the oxidic catalyst to be used can be optimized in each of the two oxidation zones. Thus, a catalyst based on multimetal oxides comprising the element combination Mo—Bi—Fe is generally preferred for the first oxidation zone (propylene→acrolein), while catalysts based on multimetal oxides comprising the element combination Mo—V are normally preferred for the second oxidation zone (acrolein→acrylic acid).

Many appropriate multimetal oxide catalysts for the two oxidation zones have been described in the past and are well-known to those skilled in the art. For example, EP-A 253 409 refers on page 5 to appropriate US patents.

Suitable catalysts for the two oxidation zones are also disclosed by DE-A 4 431 957 and DE-A 4431949. These are particularly those of the formula I in the two abovementioned documents.

For the first step of the partial oxidation, viz. the heterogeneously catalyzed gas-phase partial oxidation of propylene to acrolein, it is in principle possible to employ, as already stated, all multimetal oxide compositions comprising Mo, Bi and Fe.

These are, in particular, the active multimetal oxide compositions of the formula I of DE-A 19955176, the active multimetal oxide compositions of the formula I of DE-A 19948523, the active multimetal oxide compositions of the formula I of DE-A 19948523, the active multimetal oxide compositions of the formulae I, II and III of DE-A 10101695, the active multimetal oxide compositions of the formulae I, II and III of DE-A 19948248 and the active multimetal oxide compositions of the formulae I, II and III of DE-A 19955168 and also the active multimetal oxide compositions described in EP-A 700714.

Further multimetal oxide catalysts comprising Mo, Bi and Fe which are suitable for this oxidation step are those disclosed in DE-A 10046957, DE-A 10063162, DE-C 3338380, DE-A 19902562, EP-A 15565, DE-C 2380765, EP-A 807465, EP-A 279374, DE-A 3300044, EP-A 575897, U.S. Pat. No. 4,438,217, DE-A 19855913, WO 98/24746, DE-A 19746210 (those of the formula II), JP-A 91/294239, EP-A 293224 and EP-A 700714. This applies particularly to the embodiments mentioned by way of example in these documents, among which those of EP-A 15565, EP-A 575897, DE-A 19746210 and DE-A 19855913 are particularly preferred. In this context, particular mention may be made of a catalyst described in Example 1c of EP-A 15565 and a catalyst which can be prepared in a similar manner but whose active composition has the formula $Mo_{12}Ni_{6.5}Zn_2Fe_2Bi_1P_{0.0065}K_{0.06}O_x \cdot 10SiO_2$. Further catalysts worthy of particular mention are the Example No. 3 from DE-A 19855913 (stoichiometry: $Mo_{12}CO_7Fe_3Bi_{0.6}K_{0.08}Si_{1.6}O_x$) as all-active hollow cylinder catalyst of the geometry 5 mm×3 mm×2 mm (external diameter×height×internal diameter) and also the multimetal oxide II—all-active catalyst described in Example 1 of DE-A 19746210. Mention may also be made of the multimetal oxide catalysts of U.S. Pat. No. 4,438,217. The latter applies particularly when these hollow cylinders have a geometry of 5.5 mm×3 mm×3.5 mm or 5 mm×2 mm×2 mm or 5 mm×3 mm×2 mm or 6 mm×3 mm×3 mm or 7 mm×3 mm×4 mm (in each case external diameter×height×internal diameter).

Many of the active multimetal oxide compositions suitable for the step from propylene to acrolein can be described by the formula IV

$$Mo_{12}Bi_aFe_bX_c^1X_d^2X_e^3X_f^4O_n, \qquad (IV)$$

where the variables have the following meanings:
$X^1$=nickel and/or cobalt,
$X^2$=thallium, an alkali metal and/or an alkaline earth metal,
$X^3$=zinc, phosphorus, arsenic, boron, antimony, tin, cerium, lead and/or tungsten,
$X^4$=silicon, aluminum, titanium and/or zirconium,
a=0.5 to 5,
b=0.01 to 5, preferably from 2 to 4,
c=0 to 10, preferably from 3 to 10,
d=0 to 2, preferably from 0.02 to 2,
e=0 to 8, preferably from 0 to 5,
f=0 to 10 and
n=a number determined by the valence and abundance of the elements other than oxygen in IV.

They are obtainable in a manner known per se (cf., for example, DE-A 4023239) and are usually shaped in undiluted form to produce spheres, rings or cylinders or are used in the form of coated catalysts, i.e. preshaped, inert support bodies coated with the active composition. Of course, they can also be employed as catalysts in powder form.

Active compositions of the formula IV can in principle be prepared in a simple manner by producing a very intimate, preferably finely divided dry mix having a composition corresponding to their stoichiometries from suitable sources of their elemental constituents and calcining this at from 350 to 650° C. The calcination can be carried out either under inert gas or under an oxidizing atmosphere such as air (mixture of inert gas and oxygen) or under a reducing atmosphere (e.g. mixture of inert gas, $NH_3$, CO and/or $H_2$). The calcination time can be from a few minutes to a few hours and usually decreases as the temperature increases. Possible sources of the elemental constituents of the active multimetal oxide compositions IV are oxides and/or compounds which can be converted into oxides by heating, at least in the presence of oxygen.

Apart from oxides, further suitable starting compounds are, in particular, halides, nitrates, formates, oxalates, citrates, acetates, carbonates, amine complexes, ammonium salts and/or hydroxides (compounds such as $NH_4OH$, $(NH_4)_2CO_3$, $NH_4NO_3$, $NH_4CHO_2$, $CH_3COOH$, $NH_4CH_3CO_2$ and/or ammonium oxalate which decompose and/or can be decomposed to compounds which are given off in gaseous form at the latest during the subsequent calcination can additionally be incorporated in the intimate dry mix).

The intimate mixing of the starting compounds for preparing active multimetal oxide compositions IV can be carried out dry or wet. If it is carried out dry, the starting compounds are advantageously used as fine powders and are subjected to calcination after mixing and, if appropriate, compaction. However, the intimate mixing is preferably carried out wet. In this case, the starting compounds are usually mixed with one another in the form of aqueous solutions and/or suspensions. Particularly intimate dry mixes are obtained in the mixing process described when the sources of the elemental constituents are all in dissolved form. Water is preferably used as solvent. The aqueous composition obtained is subsequently dried, preferably by spray drying the aqueous mixture at outlet temperatures of from 100 to 150° C.

The active multimetal oxide compositions of the formula IV can be used either in powder form or after shaping to particular catalyst geometries for the "propene→acrolein" step. Shaping can be carried out before or after final calcination. For example, all-active catalysts can be produced from the powder form of the active composition or its uncalcined and/or partially calcined precursor composition by compaction to give the desired catalyst geometry (e.g. by tableting, extrusion or ram extrusion), with auxiliaries such as graphite or stearic acid as lubricants and/or shaping aids and reinforcing materials such as microfibers of glass, asbestos, silicon carbide or potassium titanate being able to be added if desired. Suitable all-active catalyst geometries are, for example, solid cylinders or hollow cylinders having an external diameter and a length of from 2 to 10 mm. In the case of hollow cylinders, a wall thickness of from 1 to 3 mm is advantageous. Of course, the all-active catalyst can also have a spherical geometry, in which case the diameter can be from 2 to 10 mm.

A particularly useful hollow cylinder geometry is 5 mm×3 mm×2 mm (external diameter×length×internal diameter), especially in the case of all-active catalysts.

Of course, shaping of the pulverulent active composition or its pulverulent, not yet calcined and/or partially calcined, precursor composition can also be achieved by application to preshaped inert catalyst supports. Coating of the support bodies for producing coated catalysts is generally carried out in a suitable rotatable container, as is known, for example, from DE-A 2909671, EP-A 293859 or EP-A 714700. To coat the support bodies, the powder composition to be applied is advantageously moistened and dried again after application, e.g. by means of hot air. The thickness of the layer of powder composition applied to the support body is advantageously in the range from 10 to 1000 μm, preferably in the range from 50 to 500 μm and particularly preferably in the range from 150 to 250 μm.

As support materials, it is possible to use customary porous or nonporous aluminum oxides, silicon dioxide, thorium dioxide, zirconium dioxide, silicon carbide or silicates such as magnesium silicate or aluminum silicate. They are generally essentially inert in respect of the target reaction in the process of the present invention. The support bodies can have regular or irregular shapes, but regularly shaped support bodies having a significant surface roughness, e.g. spheres or hollow cylinders, are preferred. The use of essentially nonporous, spherical steatite supports which have a rough surface and a diameter of from 1 to 8 mm, preferably from 4 to 5 mm, can be appropriate. However, the use of cylinders having a length of from 2 to 10 mm and an external diameter of from 4 to 10 mm as support bodies can also be appropriate. In the case of suitable rings as support bodies, the wall thickness is usually from 1 to 4 mm. Ring-shaped support bodies preferred for the purposes of the present invention have a length of from 2 to 6 mm, an external diameter of from 4 to 8 mm and a wall thickness of from 1 to 2 mm. Rings having the geometry 7 mm×3 mm×4 mm (external diameter×length×internal diameter) are also particularly useful as support bodies according to the present invention. It goes without saying that the fineness of the catalytically active oxide compositions to be applied to the surface of the support body is matched to the desired thickness of the coating (cf. EP-A 714 700).

Further active multimetal oxide compositions which can be used for the step from propylene to acrolein are compositions of the formula V

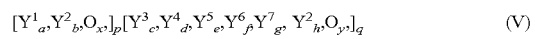 (V)

where the variables have the following meanings:
$Y^1$=bismuth alone or bismuth and at least one of the elements tellurium, antimony, tin and copper,
$Y^2$=molybdenum or molybdenum and tungsten,
$Y^3$=an alkali metal, thallium and/or samarium,
$Y^4$=an alkaline earth metal, nickel, cobalt, copper, manganese, zinc, tin, cadmium and/or mercury,
$Y^5$=iron or iron and at least one of the elements chromium and cerium,
$Y^6$=phosphorus, arsenic, boron and/or antimony,
$Y^7$=a rare earth metal, titanium, zirconium, niobium, tantalum, rhenium, ruthenium, rhodium, silver, gold, aluminum, gallium, indium, silicon, germanium, lead, thorium and/or uranium,
a'=0.01 to 8,
b'=0.1 to 30,
c'=0 to 4,
d'=0 to 20,
e'>0 to 20,
f'=0 to 6,
g'=0 to 15,
h'=8 to 16,
x',y'=numbers which are determined by the valence and abundance of the elements other than oxygen in V and
p,q=numbers whose ratio p/q is from 0.1 to 10, having three-dimensional regions of the chemical composition $Y^1{}_{a'}$, $Y^2{}_{b'}$, $O_{x'}$, which are delineated from their local environment by having a composition different from their local environment and whose maximum diameter (longest connecting line running between two points on the surface (boundary) of the region and going through the center of gravity) is from 1 nm to 100 μm, frequently from 10 nm to 500 nm or from 1 μm to 50 or 25 μm.

Particularly advantageous multimetal oxide compositions V are those in which $Y^1$ is bismuth alone.

Among these, preference is in turn given to those having the formula VI

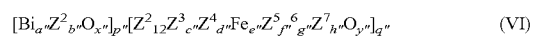 (VI)

where the variables have the following meanings:
$Z^2$=molybdenum or molybdenum and tungsten,
$Z^3$=nickel and/or cobalt,
$Z^4$=thallium, an alkali metal and/or an alkaline earth metal,
$Z^5$=phosphorus, arsenic, boron, antimony, tin, cerium and/or lead,
$Z^6$=silicon, aluminum, titanium and/or zirconium,
$Z^7$=copper, silver and/or gold,
a"=0.1 to 1,
b"=0.2 to 2,
c"=3 to 10,
d"=0.02 to 2,
e"=0.01 to 5, preferably from 0.1 to 3,
f"=0 to 5,
g"=0 to 10,
h"=0 to 1,
x",y"=numbers which are determined by the valence and abundance of the elements other than oxygen in VI,
p",q"=numbers whose ratio p"/q" is from 0.1 to 5, preferably from 0.5 to 2, with very particular preference being given to compositions VI in which $Z^2{}_{b''}$=(tungsten)$_{b''}$ and $Z^2{}_{12}$=(molybdenum)$_{12}$.

It is also advantageous for at least 25 mol % (preferably at least 50 mol % and particularly preferably at least 100 mol %) of the total $[Y^1{}_a, Y^2{}_b, O_x]_p$ content ($[Bi_{a''}Z^2{}_{b''}O_{x''}]_{p''}$) of the oxide compositions V (multimetal oxide compositions VI) suitable for the purposes of the present invention to be present in the form of three-dimensional regions of the chemical composition $Y^1{}_a, Y^2{}_b, O_x, [Bi_{a''}Z^2{}_{b''}O_{x''}]$ which are delineated from their local environment by having a chemical composition different from their local environment and whose maximum diameter is in the range from 1 nm to 100 μm.

As regards shaping, what has been said in respect of multimetal oxide catalysts IV applies to the multimetal oxide catalysts V.

The preparation of active multimetal oxide compositions V is described, for example, in EP-A 575897 and in DE-A 19855913.

The inert support materials recommended above can also be used, inter alia, as inert materials for diluting and/or bounding the appropriate fixed catalyst beds or as an upstream bed to protect the catalysts and/or heat the gas mixture.

At this point, it may be pointed out that all catalysts and multimetal oxide compositions which have been recommended as suitable for the step from propylene to acrolein are in principle also suitable for the partial ammoxidation of propylene to acrylonitrile.

For the second step, namely the heterogeneously catalyzed gas-phase partial oxidation of acrolein to acrylic acid, it is in principle possible, as mentioned above, to use all multimetal oxide compositions comprising Mo and V as active compositions, e.g. those from DE-A 10046928.

Many such compositions, e.g. those of DE-A 19815281, can be described by the formula VII

 (VII), where the variables have the following meanings:
$X^1$=W, Nb, Ta, Cr and/or Ce,
$X^2$=Cu, Ni, Co, Fe, Mn and/or Zn,
$X^3$=Sb and/or $B^1$,
$X^4$=one or more alkali metals,
$X^5$=one or more alkaline earth metals,
$X^6$=Si, Al, Ti and/or Zr,
a=1 to 6,
b=0.2 to 4,
c=0.5 to 18,
d=0 to 40,
e=0 to 2,
f=0 to 4,
g=0 to 40 and
n=a number which is determined by the valence and abundance of the elements other than oxygen in VII.

Among the active multimetal oxides VII, embodiments preferred according to the present invention are those in which the variables of the formula VII have the following meanings:
$X^1$=W, Nb and/or Cr,
$X^2$=Cu, Ni, Co and/or Fe,
$X^3$=Sb,
$X^4$=Na and/or K,
$X^5$=Ca, Sr and/or Ba,
$X^6$=Si, Al and/or Ti,
a=1.5 to 5,
b=0.5 to 2,
c=0.5 to 3,
d=0 to 2,
e=0 to 0.2,
f=0 to 1 and
n=a number which is determined by the valence and abundance of the elements other than oxygen in VII.

However, multimetal oxides VII which are very particularly preferred according to the present invention are those of the formula VIII

 (VIII)

where
$Y^1$=w and/or Nb,
$Y^2$=Cu and/or Ni,
$Y^5$=Ca and/or Sr,
$Y^6$=Si and/or Al,
a'=2 to 4,
b'=1 to 1.5,
c'=1 to 3,
f'=0 to 0.5,
g'=0 to 8 and
n'=a number which is determined by the valence and abundance of the elements other than oxygen in VIII.

The active multimetal oxide compositions (VII) which are suitable for the purposes of the present invention can be obtained in a manner known per se, e.g. that disclosed in DE-A 4335973 or in EP-A 714700.

Active multimetal oxide compositions suitable for the step "acrolein→acrylic acid", in particular ones of the formula VII, can in principle be prepared in a simple manner by producing a very intimate, preferably finely divided dry mix having a composition corresponding to their stoichiometries from suitable sources of their elemental constituents and calcining this at from 350 to 600° C. The calcination can be carried out either under inert gas or under an oxidizing atmosphere such as air (mixture of inert gas and oxygen) or under a reducing atmosphere (e.g. mixtures of inert gas and reducing gases such as $H_2$, $NH_3$, CO, methane and/or acrolein or the reducing gases mentioned on their own). The calcination time can be from a few minutes to a few hours and usually decreases as the temperature increases. Possible sources of the elemental constituents of the active multimetal oxide compositions VII are oxides and/or compounds which can be converted into oxides by heating, at least in the presence of oxygen.

The intimate mixing of the starting compounds for preparing multimetal oxide compositions VII can be carried out dry or wet. If it is carried out dry, the starting compounds are advantageously used as fine powders and are subjected to calcination after mixing and, if appropriate, compaction. However, the intimate mixing is preferably carried out wet. In this case, the starting compounds are usually mixed with one another in the form of aqueous solutions and/or suspensions. Particularly intimate dry mixes are obtained in the mixing process described when the sources of the elemental constituents are all in dissolved form. Water is preferably used as solvent. The aqueous composition obtained is subsequently dried, preferably by spray drying the aqueous mixture at outlet temperatures of from 100 to 150° C.

The resulting multimetal oxide compositions, in particular those of the formula VII, can be used for the acrolein oxidation either in powder form or after shaping to particular catalyst geometries. Shaping can be carried out before or after final calcination. For example, all-active catalysts can be produced from the powder form of the active composition or its uncalcined precursor composition by compaction to give the desired catalyst geometry (e.g. by tableting, extrusion or ram extrusion), with auxiliaries such as graphite or stearic acid as lubricants and/or shaping aids and reinforcing materials such as microfibers of glass, asbestos, silicon carbide or potassium titanate being able to be added if desired. Suitable all-active catalyst geometries are, for example, solid cylinders or hollow cylinders having an external diameter and a length of from 2 to 10 mm. In the case of hollow cylinders, a wall thickness of from 1 to 3 mm is advantageous. Of course, the all-active catalyst can also have a spherical geometry, in which case the diameter can be from 2 to 10 mm.

Of course, shaping of the pulverulent active composition or its pulverulent, not yet calcined, precursor composition can also be achieved by application to preshaped inert catalyst supports. Coating of the support bodies for producing coated catalysts is generally carried out in a suitable rotatable container, as is known, for example, from DE-A 2909671, EP-A 293859 or EP-A 714700.

To coat the support bodies, the powder composition to be applied is advantageously moistened and dried again after application, e.g. by means of hot air. The thickness of the layer of powder composition applied to the support body is advantageously in the range from 10 to 1000 µm, preferably in the range from 50 to 500 µm and particularly preferably in the range from 150 to 250 µm.

As support materials, it is possible to use customary porous or nonporous aluminum oxides, silicon dioxide, thorium dioxide, zirconium dioxide, silicon carbide or silicates such as magnesium silicate or aluminum silicate. The support bodies can have regular or irregular shapes, but regularly shaped support bodies having a significant surface roughness, e.g. spheres or hollow cylinders having a grit coating, are preferred. The use of essentially nonporous, spherical steatite supports which have a rough surface and a diameter of from 1 to 8 mm, preferably from 4 to 5 mm, can be appropriate. However, the use of cylinders having a length of from 2 to 10 mm and an external diameter of from 4 to 10 mm as support bodies can also be appropriate. In the case of rings as support bodies, the wall thickness is usually from 1 to 4 mm. Ring-shaped support bodies preferably have a length of from 2 to 6 mm, an external diameter of from 4 to 8 mm and a wall thickness of from 1 to 2 mm. Rings having the geometry 7 mm×3 mm×4 mm (external diameter×length×internal diameter) are also particularly useful as support bodies. It goes without saying that the fineness of the catalytically active oxide compositions to be applied to the surface of the support body is matched to the desired thickness of the coating (cf. EP-A 714 700).

Advantageous active multimetal oxide compositions to be used for the step "acrolein→acrylic acid" are compositions which have the formula IX, $$[D]_p[E]_q \quad (IX),$$

where the variables have the following meanings:
$D = Mo_{12}V_{a''}Z^1_{b''}Z^2_{c''}Z^3_{d''}Z^4_{e''}Z^5_{f''}Z^6_{g''}O_{x'''}$,
$E = Z^7_{12}Cu_{h''}H_{i''}O_{y''}$,
$Z^1$ = W, Nb, Ta, Cr and/or Ce,
$Z^2$ = Cu, Ni, Co, Fe, Mn and/or Zn,
$Z^3$ = Sb and/or $B^1$,
$Z^4$ = Li, Na, K, Rb, Cs and/or H,
$Z^5$ = Mg, Ca, Sr and/or Ba,
$Z^6$ = Si, Al, Ti and/or Zr,
$Z^7$ = Mo, W, V, Nb and/or Ta, preferably Mo and/or W,
a″ = 1 to 8,
b″ = 0.2 to 5,
c″ = 0 to 23,
d″ = 0 to 50,
e″ = 0 to 2,
f″ = 0 to 5,
g″ = 0 to 50,
h″ = 4 to 30,
i″ = 0 to 20 and
x″,y″ = numbers which are determined by the valence and abundance of the elements other than oxygen in IX and
p,q = nonzero numbers whose ratio p/q is from 160:1 to 1:1, and are obtainable by separately preforming a multimetal oxide composition E, $$Z^7_{12}Cu_{h''}H_{i''}O_{y''} \quad (E),$$

in finely divided form (starting composition 1) and subsequently incorporating the preformed solid starting composition 1 into an aqueous solution, an aqueous suspension or a finely divided dry mix of sources of the elements Mo, V, $Z^1$, $Z^2$, $Z^3$, $Z^4$, $Z^5$ and $Z^6$ containing the abovementioned elements in the stoichiometry D, $$Mo_{12}V_{a''}Z^1_{b''}Z^2_{c''}Z^3_{d''}Z^4_{e''}Z^5_{f''}Z^6_{g''} \quad (D),$$

(starting composition 2) in the desired ratio p:q, if necessary drying the resulting aqueous mixture and calcining the dry precursor composition obtained in this way at from 250 to 600° C. to give the desired catalyst geometry.

Preference is given to multimetal oxide compositions IX prepared by incorporating the preformed solid starting composition 1 into an aqueous starting composition 2 at ≦70° C. A detailed description of the preparation of multimetal oxide catalysts IX may be found, for example, in EP-A 668104, DE-A 19736105, DE-A 10046928, DE-A 19740493 and DE-A 19528646.

With regard to shaping, what has been said in respect of the multimetal oxide catalysts VII applies to the multimetal oxide catalysts IX.

Further multimetal oxide catalysts which are very useful for the step "acrolein→acrylic acid" are those of DE-A 19815281, in particular active multimetal oxide compositions of the formula I described in that document.

It is advantageous to use all-active catalyst rings for the step from propylene to acrolein and coated catalyst rings for the step from acrolein to acrylic acid.

The first step of the partial oxidation, from propylene to acrolein, can be carried out using the above-described catalysts in, for example, a single-zone multitube fixed-bed reactor as described in DE-A 4431957.

Oxygen is used as oxidant. If $N_2$ is chosen as inert diluent gas, the use of air as oxygen source is particularly advantageous.

The partial oxidation is generally carried out at a propylene:oxygen:inert gas (including water vapor) volume (standard l) ratio of 1:(1.0–3.0):(5–25), preferably 1:(1.7–2.3):(10–15). The reaction pressure is usually in the range from 1 to 3 bar and the total space velocity is preferably from 1500 to 4000 standard l/(l·h). The space velocity of propylene is typically from 90 to 200 standard l/(l·h).

The feed gas mixture preferably flows into the single-zone multitube fixed-bed reactor from above. As heat transfer medium, it is advantageous to use a salt melt, preferably one consisting of 60% by weight of potassium nitrate ($KNO_3$) and 40% by weight of sodium nitrite ($NaNO_2$) or of 53% by weight of potassium nitrate ($KNO_3$), 40% by weight of sodium nitrite ($NaNO_2$) and 7% by weight of sodium nitrate ($NaNO_3$).

Viewed over the reactor, salt melt and reaction gas mixture can be conveyed either in cocurrent or in countercurrent. The salt melt is preferably passed around the catalyst tubes in a meandering fashion.

If the feed mixture is passed through the catalyst tubes from the top downward, it is advantageous to charge the catalyst tubes as follows from the bottom upward (if flow is from the bottom upward, the charge sequence is advantageously reversed):

firstly for a length of from 40 to 60% of the catalyst tube length, either only catalyst or a mixture of catalyst and inert material, with the latter making up up to 20% by weight, based on the mixture (section C);

subsequently for a length of from 20 to 40% of the total tube length, either only catalyst or a mixture of catalyst and inert material, with the latter making up up to 40% by weight, based on the mixture (section B); and finally for a length of from 10 to 20% of the total tube length, a bed of inert material (section A) which is preferably chosen so that it produces a very small pressure drop.

Section C is Preferably Undiluted.

The abovementioned charge variant is particularly advantageous when catalysts as described in Example 1 of DE-A 10046957 or as described in Example 3 of DE-A 10046957 are used and steatite rings having the geometry 7 mm×7 mm×4 mm (external diameter×height×internal diameter) are used as inert material. As regards the salt bath temperature, what is said in DE-A 4431957 applies.

The first step of the partial oxidation, from propylene to acrolein, can also be carried out using the catalysts described but in, for example, a two-zone multitube fixed-bed reactor as described in DE-A 19910506. In both the above-described cases, the propene conversion achieved in a single pass is normally ≧90 mol % or ≧95 mol %. The second step of the partial oxidation, from acrolein to acrylic acid, can be carried out using the catalysts described in, for example, a single-zone multitube fixed-bed reactor as described in DE-A 4431949. In general, the product mixture from the oxidation of propylene to acrolein is passed as such (if desired after intermediate cooling), i.e. without secondary components being separated off, to the oxidation of acrolein to acrylic acid.

The oxygen required for the second step of the partial oxidation is preferably added as air and is generally added directly to the product gas mixture from the propylene oxidation.

In general, the feed gas mixture to such an acrolein oxidation then has the following composition: acrolein:oxygen:water vapor:inert gas volume ratio (standard l) of 1:(1–3):(0–20):(3–30), preferably from 1:(1–3):(0.5–10):(7–18).

Here too, the reaction pressure is generally from 1 to 3 bar and the total space velocity is preferably from 1000 to 3800 standard l/(l·h). The space velocity of acrolein is typically from 80 to 190 standard l/(l·h).

The feed gas mixture preferably likewise flows into the single-zone multitube fixed-bed reactor from above. In the second stage too, the heat transfer medium used is advantageously a salt melt, preferably one consisting of 60% by weight of potassium nitrate ($KNO_3$) and 40% by weight of sodium nitrite ($NaNO_2$) or of 53% by weight of potassium nitrate ($KNO_3$), 40% by weight of sodium nitrite ($NaNO_2$) and 7% by weight of sodium nitrate ($NaNO_3$). Viewed over the reactor, salt melt and reaction gas mixture can be conveyed either in cocurrent or in countercurrent. The salt melt is preferably passed around the catalyst tubes in a meandering fashion.

If the feed mixture is passed through the catalyst tubes from the top downward, it is advantageous to charge the catalyst tubes as follows from the bottom upward:

firstly for a length of from 50 to 70% of the catalyst tube length, either only catalyst or a mixture of catalyst and inert material, with the latter making up up to 20% by weight, based on the mixture (section C);

subsequently for a length of from 20 to 40% of the total tube length, either only catalyst or a mixture of catalyst and inert material, with the latter making up up to 40% by weight, based on the mixture (section B); and finally for a length of from 5 to 20% of the total tube length, a bed of inert material (section A) which is preferably chosen so that it produces a very small pressure drop.

Section C is Preferably Undiluted.

If flow through the catalyst tubes is from the bottom upward, the charge sequence in the catalyst tubes is advantageously reversed.

The abovementioned charge variant is particularly advantageous when catalysts as described in preparative Example 5 of DE-A 10046928 or as described in DE-A 19815281 are used and steatite rings having the geometry 7 mm×7 mm×4 mm or 7 mm×7 mm×3 mm (in each case external diameter×height×internal diameter) are used as inert material. As regards the salt bath temperature, what is said in DE-A 44 319 49 applies. It is generally selected so that the acrolein conversion achieved in a single pass is normally ≧90 mol % or ≧95 mol %.

The second step of the partial oxidation, from acrolein to acrylic acid, can also be carried out using the catalysts described but in, for example, a two-zone multitube fixed-bed reactor as described in DE-19910508. As regards the acrolein conversion, what has been said above applies. When this second step is carried out in a two-zone multitube fixed-bed reactor, the product gas mixture from a partial oxidation directed at the first step (as has been described above) is likewise advantageously used directly (if desired after intermediate cooling) for producing the feed gas mixture. The oxygen required for the second step of the partial oxidation is preferably added as air and in the second case added directly to the product gas mixture from the first step of the partial oxidation.

In a two-stage mode of operation with direct further use of the product gas mixture from the first step of the partial oxidation for supplying the second step of the partial oxidation, two single-zone multitube fixed-bed reactors or two two-zone multitube fixed-bed reactors are generally connected in series. A mixed connection in series (single-zone/two-zone or vice versa) is also possible.

An intermediate cooler which may, if desired, contain inert beds which can perform a filtering function can be located between the reactors. The salt bath temperature of multitube reactors for the first step of the partial oxidation from propylene to acrylic acid is generally from 300 to 400° C. The salt bath temperature of multitube reactors for the second step of the partial oxidation from propylene to acrylic acid, viz. the partial oxidation of acrolein to acrylic acid, is usually from 200 to 350° C. In addition, the heat transfer media (preferably salt melts) are normally conveyed through the relevant multitube fixed-bed reactors in such amounts that the difference between their inflow temperature and their outflow temperature is generally ≦5° C. As mentioned above, both steps of the partial oxidation of propylene to acrylic acid can also be brought about over one charge in one reactor as described in DE-A 10121592.

It may be mentioned once again that part of the feed gas mixture (gas mixture 2) for the first step ("propylene→acrolein") can be recycle gas from the partial oxidation.

This is gas which remains after the target product(s) has/have been separated off (acrolein and/or acrylic acid separation) from the product gas mixture from the partial oxidation and can be recirculated as inert diluent gas to the feed to the first and/or second step of the partial oxidation of propylene to acrolein and/or acrylic acid.

However, such recycle gas comprising propane and possibly propylene is preferably recirculated to the feed to the first step of the process of the present invention.

It may also be mentioned once again that a partial oxidation and/or ammoxidation according to the present invention can be carried out by firstly passing a reaction gas mixture containing no oxygen over the catalyst charge. In this case, the oxygen required for the partial oxidation is made available as lattice oxygen. The catalyst bed is regenerated in a subsequent regeneration step using an oxygen-containing gas (e.g. air, oxygen-enriched air or oxygen-depleted air) so that it is then once again available for an oxygen-free reaction gas mixture, and so forth.

In summary, a shell-and-tube reactor in which the catalyst charge alters along the individual catalyst tubes at the end of the first reaction step (such propylene partial oxidations suitable as reaction zone B according to the present invention are taught by, for example, EP-A 911313, EP-A 979813, EP-A 990636 and DE-A 2830765) represents the simplest way of realizing two oxidation zones for the two steps of the partial oxidation of propylene to acrylic acid. If desired, the catalyst charge in the catalyst tubes is interrupted by an inert bed.

However, the two oxidation zones are preferably realized in the form of two shell-and-tube systems connected in series. These can be located in one reactor, with the transition from one bundle of tubes to the other bundle of tubes being formed by a bed of inert material which is not accommodated in the catalyst tube (and is advantageously accessible). While a heat transfer medium generally flows around the catalyst tubes, it does not reach an inert bed installed as described above. The two bundles of catalyst tubes are therefore advantageously accommodated in reactors which are physically separate from one another. In general, an intermediate cooler is located between the two shell-and-tube reactors in order to reduce any after-combustion of acrolein in the product gas mixture leaving the first oxidation zone. In place of shell-and-tube reactors, it is also possible to use plate heat exchanger reactors with salt cooling and/or evaporative cooling, as are described, for example, in DE-A 19 929 487 and DE-A 19 952 964.

The reaction temperature in the first oxidation zone is generally from 300 to 450° C., preferably from 320 to 390° C. The reaction temperature in the second oxidation zone is generally from 200 to 300° C., frequently from 220 to 290° C. The reaction pressure in the two oxidation zones is advantageously from 0.5 to 5 atm, preferably from 1 to 3 atm. The space velocity (standard l/l·h) of the reaction gas over the oxidation catalysts in both oxidation zones is frequently from 1500 to 2500 $h^{-1}$ or up to 4000 $h^{-1}$. The space velocity of propylene can be from 100 to 200 and more standard l/l·h.

In principle, the two oxidation zones in the process of the present invention can be configured as described, for example, in DE-A 19 837 517, DE-A 19 910 506, DE-A 19 910 508 and DE-A 19 837 519. The external heating in the two oxidation zones, if desired in multizone reactor systems, is usually matched in a manner known per se to the specific reaction gas mixture composition and the catalyst charge.

The total molecular oxygen needed as oxidant for the partial zone or zones required according to the present invention can all be added at the beginning to the feed gas mixture fed into the partial zone or zones. However, it is of course also possible, e.g. in the preparation of acrylic acid, to add additional oxygen after the first partial zone. This latter procedure is preferred in the case of the preparation of acrylic acid.

In the first oxidation zone (propylene→acrolein), a molar ratio of propylene:molecular oxygen of 1:1–3, frequently 1:1.5–2, is set. Similar numerical values are suitable for the molar ratio of acrolein:molecular oxygen in the second oxidation zone (1:0.5–1.5 would be preferred) for the partial oxidation of acrolein to acrylic acid.

In both oxidation zones, an excess of molecular oxygen generally has an advantageous effect on kinetics of the gas-phase oxidation. In contrast to the ratios in the dehydrogenation employed according to the present invention, the thermodynamic conditions in the partial oxidation or oxdations are not influenced significantly by the molar ratio of reactants, since the heterogeneously catalyzed gas-phase partial oxidation of propylene to acrylic acid is kinetically controlled. In principle, therefore, the propylene can also be employed in a molar excess over molecular oxygen, e.g. in the first oxidation zone. In this case, the excess propylene acts as a diluent gas.

However, the heterogeneously catalyzed gas-phase partial oxidation of propylene to acrylic acid can in principle also be carried out in a single oxidation zone. In this case, both reaction steps occur in an oxidation reactor which is charged with a catalyst which is able to catalyze both reaction steps. It goes without saying that the catalyst charge can also alter continuously or abruptly within the oxidation zone along the reaction coordinate. In one embodiment of the partial oxidation or oxidations employed according to the invention in the form of two oxidation zones connected in series, carbon oxide and water vapor formed as by-product in the first oxidation zone and present in the product gas mixture leaving the first oxdation zone can, if required, naturally be partly or completely separated off from this product gas mixture before it is passed to the second oxidation zone. According to the present invention, preference is given to a mode of operation which does not require such a separation.

Possible sources of the molecular oxygen required for the partial oxidation(s) and/or ammoxidation(s), which is mixed with the gas mixture 1 or 1' before the latter is fed into the partial zone, include both pure molecular oxygen and molecular oxygen diluted with inert gas such as $CO_2$, CO, noble gases, $N_2$ and/or saturated hydrocarbons.

Air is advantageously used as oxygen source to cover at least part of the molecular oxygen requirement.

Introduction of cold air into the hot gas mixture 1 or 1' in the process of the present invention can effect direct cooling of the gas mixture 1 or 1'.

The product gas mixture leaving the partial zone employed according to the invention in the case of a preparation of acrolein and/or acrylic acid is generally composed essentially of the target product acrolein or acrylic acid or a mixture of the latter with acrolein, unreacted molecular oxygen, propane, unreacted propylene, molecular nitrogen, water vapor formed as by-product and/or used as diluent gas, carbon oxides formed as by-product and/or used as diluent gas and also small amounts of other lower aldehydes, lower alkanecarboxylic acids (e.g. acetic acid, formic acid and propionic acid) and maleic anhydride, benzaldehyde, aromatic carboxylic acids and aromatic carboxylic anhydrides (e.g. phthalic anhydride and benzoic acid), possibly further hydrocarbons such as $C_4$-hydrocarbons (e.g. 1-butene and possibly other butenes) and other inert diluent gases.

The target product can be separated off from the product gas mixture in a manner known per se (e.g. by partial condensation of acrylic acid or by absorption of acrylic acid in water or in a high-boiling hydrophobic organic solvent or by absorption of acrolein in water or in aqueous solutions of lower carboxylic acids and subsequent work-up of the absorbates; alternatively, the product gas mixture can also be fractionally condensed; cf., for example, EP-A 117146, DE-A 4308087, DE-A 4335172, DE-A 4436243, DE-A 19 924 532 and DE-A 19 924 533). Acrylic acid can also be separated off as described in EP-A 982287, EP-A 982289, DE-A 19924532, DE-A 10115277, DE-A 19606877, DE-A 19740252, DE-A 19627847, DE-A 10053086 and EP-A 982288.

Unreacted propylene and/or acrolein are, if desired, likewise separated off and recirculated to the partial zone.

The separation is preferably carried out as in FIG. 7 of WO/0196271. Otherwise, significant constituents other than acrylic acid and acrolein in the residual gas remaining after the target product has been separated off, crude propane used and dehydrogenation/oxydehydrogenation catalyst used can each be separated off separately and/or be recirculated together with the propane and recycle gas (recirculation stream) to the feed to the first step of the process of the present invention. However, the unreacted propane can of course also be recirculated in admixture with the unreacted propylene (as feed circulation stream) to this feed stream. In a continuous embodiment of the process of the present invention, propane is thus converted continuously into acrylic acid and/or acrolein.

Propane and propene can, as described above, be separated off from the residual gas remaining after the target product has been separated off (which generally comprises $O_2$, CO, $CO_2$, $H_2O$, $N_2$, noble gases and also other lower aldehydes, lower alkanecarboxylic acids (e.g. acetic acid, formic acid and propionic acid) and maleic anhydride, benzaldehyde, aromatic carboxylic acids and aromatic carboxylic anhydrides (e.g. phthalic anhydride and benzoic acid) and hydrocarbons, e.g. $C_4$-hydrocarbons (e.g. 1-butene and possibly other butenes)) by absorption in a high-boiling hydrophobic organic solvent with subsequent desorption and/or stripping (and reuse of absorption medium). Further possible ways of achieving the separation are adsorption, rectification, membrane processes and partial condensation. The separation processes mentioned are preferably carried out at superatmospheric pressure.

When dehydrogenation catalysts which are sensitive to oxygen or oxygen-containing compounds are used, these oxygen compounds are separated off from the recycle gas before the latter is recirculated to the feed to the first step of the process of the present invention. Such a removal of oxygen can also be useful to avoid total oxidation of propane in the dehydrogenation stage.

The dehydrogenation catalysts of DE-A-19 937 107 are not sensitive to oxygen compounds (in particular those described in Examples 1 to 4 of the DE first publication).

Another possible way of carrying out the separation is, as likewise mentioned above, fractional distillation. Preference is given to carrying out a fractional pressure distillation at low temperatures. The pressure employed can be, for example, from 10 to 100 bar. As rectification columns, it is possible to use columns packed with random packing, tray columns or columns containing order packing. Suitable tray columns are columns having dual-flow trays, bubble cap trays or valve trays. The reflux ratio can be, for example, from 1 to 10. Other possible ways of performing the separation are, for example, pressure extraction, pressure swing adsorption, pressure scrubbing, partial condensation and pressure extraction.

According to the present invention, it is of course also possible, e.g. when a removal of secondary components (e.g. $C_4$-hydrocarbons (e.g. 1-butene, n-butane, isobutane and possibly other butenes)) is employed after the first step of the process of the present invention or the interfering $C_4$-hydrocarbons do not accumulate (e.g. when they are burnt over suitable catalysts in the partial zone), for the total amount of residual gas to be recirculated (as recirculation stream) to the feed to the first step of the process of the present invention. In this case, the outlet for gas constituents other than propane, propylene and molecular oxygen can be exclusively between the gas mixture 1 and the gas mixture 1'.

It goes without saying that a further outlet can be provided after the target product has been separated off. If the recycle gas recirculated to a propane dehydrogenation comprises carbon monoxide, this can be subjected to catalytic combustion to $CO_2$ before fresh crude propane is added. The heat of reaction liberated can be employed for heating to the dehydrogenation temperature.

Catalytic after-combustion of CO present in the tailgas to $CO_2$ can also be advisable when the carbon oxides are to be separated off from the tailgas before it is recirculated as recycle gas to the dehydrogenation and/or oxydehydrogenation of propane, since $CO_2$ can be separated off comparatively simply (e.g. by scrubbing with a basic liquid). Such a catalytic after-combustion of CO can also be carried out in the dehydrogenation zone, e.g. over the above-described dehydrogenation catalysts (e.g. those of DE-A 19937107, in particular those described in Ex. 1 to 4 of this DE first publication).

It is naturally also possible to recirculate part of the tailgas unaltered to the dehydrogenation and/or oxydehydrogenation of propane and separating off a mixture of propane and propylene only from the remaining part and likewise recirculating this to the dehydrogenation and/or oxydehydrogenation of propane and/or to the partial zone or zones. In the latter case, the remaining part of the tailgas is advantageously combined with the gas mixture 1 or gas mixture 1'.

A fractional distillation of the tailgas can, for example, be carried out in such a way that essentially all those constituents whose boiling point is lower than the boiling point of the propylene are separated off in the ascending stripping section of the rectification column and are taken off at the top of the column. These constituents are first and foremost the carbon oxides CO and $CO_2$ together with unreacted oxygen and ethylene and also methane and $N_2$. At the bottom, higher-boiling $C_4$-hydrocarbons, for example, can be separated off.

If a heterogeneously catalyzed oxydehydrogenation of propane is employed as first step of the process of the present invention, secondary components can also be separated off whenever molecular nitrogen is separated off according to DE-A 19837520, DE-A 19837517, DE-A 19837519 and DE-A 19837518.

EXAMPLES

Heterogeneously catalyzed gas-phase partial oxidation of propylene in two fixed-bed reactors connected in series using various gas mixtures 2 comprising propylene and propane A) Description of the General Process Conditions 1. First Fixed-bed Reactor for the Step of Partial Oxidation of Propylene to Acrolein

| | |
|---|---|
| Heat transfer medium used: | salt melt consisting of 53% by weight of potassium nitrate, 40% by weight of sodium nitrite and 7% by weight of sodium nitrate. |
| Dimensions of the catalyst tube: | 4200 mm total length, 26 mm internal diameter, 30 mm external diameter, 2 mm wall thickness. |

Reactor: comprises a double-walled cylinder of stainless steel (cylindrical guide tube surrounded by a cylindrical outer container). The wall thicknesses were everywhere from 2 to 5 mm.
  The internal diameter of the outer cylinder was 168 mm. The internal diameter of the guide tube was about 60 mm.
  The double-walled cylinder was closed off by a lid and bottom at the top and bottom, respectively.
  The catalyst tube was accommodated in the cylindrical container so that its upper and lower ends projected through the lid and bottom, respectively, by 250 mm in each case (and were sealed into the lid and bottom).
  The heat transfer medium was enclosed in the cylindrical container. To ensure very uniform thermal boundary conditions at the outer wall of the catalyst tube over the entire catalyst tube length within the cylindrical container (3700 mm), the heat transfer medium was circulated by bubbling nitrogen into the cylindrical container.
  The heat transfer medium was conveyed from the bottom upward in the cylindrical guide tube by means of the ascending nitrogen and then flows back downward in the intermediate space between cylindrical guide tube and cylindrical outer container (similarly good circulation can also be achieved by pumping (e.g. propeller pumps)). The temperature of the heat transfer medium could be regulated at the desired level by means of electrical heating applied to the outer wall. Otherwise, cooling was by means of air.

| | |
|---|---|
| Feed to reactor: | Viewed over the reactor, salt melt and reaction gas mixture (the respective gas mixture 2) were conveyed in countercurrent. The reaction gas mixture entered the reactor from the top. In each case, it had a temperature of 250° C. on entering the reaction tube. The salt melt entered the cylindrical guide tube at the bottom at a temperature $T^{in}$ and left the cylindrical guide tube at the top at a temperature $T^{out}$. The difference between $T^{in}$ and $T^{out}$ was about 2° C. $T^{mean} = (T^{in} + T^{out})/2$. |
| Catalyst tube charge: (from the top downward) | Section A: 50 cm long Prebed of steatite rings having the geometry 7 mm × 7 mm × 4 mm (external diameter × length × internal diameter). Section B: 100 cm long Catalyst tube charge consisting of a homogeneous mixture of 30% by weight of steatite rings having the geometry 5 mm × 3 mm × 2 mm (external diameter × length × internal diameter) and 70% by weight of all-active catalyst from section C. Section C: 170 cm long Catalyst charge consisting of ring-shaped (5 mm × 3 mm × 2 mm = external diameter × length × internal diameter) all-active catalyst as decribed in Example 1 of DE-A 10046957. Section D: 50 cm long After-bed of steatite rings having the geometry 7 mm × 7 mm × 4 mm (external diameter × length × internal diameter). |
| Flow of reaction gas starting mixture through the reactor: | in all cases 3860 g/h of gas mixture 2. |
| Space velocity of propylene over the catalyst charge: | 100 standard liters/l · h. |

2. Description of the Intermediate Cooling and Intermediate Introduction of Oxygen The product gas mixture leaving the first fixed-bed-reactor was for the purposes of the intermediate cooling (indirectly by means of air) passed through a connecting tube (length=400 mm, internal diameter=26 mm, wall thickness =2 mm, material=stainless steel) which was charged in its central 200 mm with an inert bed of steatite spheres having a diameter of 6 mm and was connected directly by means of a flange to the catalyst tube of the first fixed-bed reactor.

In all cases, the gas mixture entered the connecting tube at a temperature of more than 310° C. and left it at a temperature of about 140° C. 290 standard liters/h of compressed air as oxygen source were subsequently mixed into the gas mixture.

The resulting feed gas mixture was fed at a temperature of 220° C. into the fixed-bed reactor for the step of the partial oxidation of-acrolein to acrylic acid.

3. Second Fixed-Bed Reactor for the Step of Partial Oxidation of Acrolein to Acrylic Acid A fixed-bed reactor which had an identical construction to that for the first step was used. Viewed over the reactor, salt melt and reaction gas mixture were conveyed in cocurrent. Both the salt melt and the reaction gas mixture entered at the bottom.

The catalyst tube charge (from the bottom upward) was:
Section A: 20 cm long
Prebed of steatite rings having the geometry
7 mm×7 mm×4 mm
(external diameter×length×internal diameter).
Section B: 100 cm long
Catalyst charge consisting of a homogeneous mixture of 30% by weight of steatite rings having the geometry
7 mm×3 mm×4 mm (external diameter×length×internal diameter) and 70% by weight of coated catalyst from section C.
Section C: 200 cm long
Catalyst charge consisting of ring-shaped
(7 mm×3 mm×4 mm=external diameter×length×internal diameter) of coated catalyst as described in preparative Example 5 of DE-A 10046928.
Section D: 50 cm long
After-bed of steatite rings having the geometry
7 mm×7 mm×4 mm
(external diameter×length×internal diameter).

A nominal 4240 g/h of feed gas mixture was in all cases passed through the second reactor. $T^{mean}$ is defined as for the first fixed-bed reactor.

In all the following examples, the propylene conversion in the first reactor was set to 97.7 mol % and the acrolein conversion in the second reactor was set to 99.3 mol %.

The $T^{mean}$ required as a function of the composition of the gas mixture 2 and also the yields $A^{AA}$ (mol %) of acrylic acid and selectivities of carbon oxide formation $S_{CO_x}$ (mol %), based on propylene reacted over both reactors, achieved as a function of the composition of the gas mixture 2 had the following values in the individual examples.

B) Example 1

The composition of the gas mixture 2 was:
6.18% by volume of propylene,
33.1% by volume of propane,
12.3% by volume of oxygen,
0.15% by volume of COX,
46.7% by volume of $N_2$ and
1.63% by volume of $H_2O$.

| $A^{AA}$ = 86.1 mol % | $T^{mean}$, 1st reactor = 316° C. |
|---|---|
| $S^{CO_x}$ = 9.2 mol % | $T^{mean}$, 2nd reactor = 274° C. |

C) Example 2

The composition of the gas mixture 2 was:
6.04% by volume of propylene,
42.3% by volume of propane,
10.4% by volume of oxygen,
0.15% by volume of $CO_x$,
39.5% by volume of $N_2$ and
1.60% by volume of $H_2O$.

| $A^{AA}$ = 85.2 mol % | $T^{mean}$, 1st reactor = 322° C. |
|---|---|
| $S^{CO_x}$ = 9.9 mol % | $T^{mean}$, 2nd reactor = 278° C. |

D) Example 3

The composition of the gas mixture 2 was:
0.20% by volume of ethane,
6.14% by volume of propylene,
33.0% by volume of propane,
12.2% by volume of oxygen,
0.16% by volume of $CO_x$,
46.6% by volume of $N_2$ and
1.65% by volume of $H_2O$.

| $A^{AA}$ = 86.1 mol % | $T^{mean}$, 1st reactor = 316° C. |
|---|---|
| $S^{CO_x}$ = 9.2 mol % | $T^{mean}$, 2nd reactor = 274° C. |

E) Example 4

The composition of the gas mixture 2 was:
0.22% by volume of ethylene,
6.13% by volume of propylene,
33.0% by volume of propane,
12.2% by volume of oxygen,
0.16% by volume of $CO_x$,
46.6% by volume of $N_2$ and
1.64% by volume of $H_2O$.

| $A^{AA}$ = 86.1 mol % | $T^{mean}$, 1st reactor = 316° C. |
|---|---|
| $S^{CO_x}$ = 9.2 mol % | $T^{mean}$, 2nd reactor = 274° C. |

F) Example 5

The composition of the gas mixture 2 was:
0.20% by volume of n-butane,
6.14% by volume of propylene,
33.0% by volume of propane,
12.2% by volume of oxygen,
0.16% by volume of $CO_x$,
46.6% by volume of $N_2$ and
1.65% by volume of $H_2O$.

| $A^{AA}$ = 85.2 mol % | $T^{mean}$, 1st reactor = 316.5° C. |
|---|---|
| $S^{CO_x}$ = 9.9 mol % | $T^{mean}$, 2nd reactor = 274° C. |

G) Example 6

The composition of the gas mixture 2 was:
2.02% by volume of n-butane,
5.98% by volume of propylene,
32.4% by volume of propane,
12.0% by volume of oxygen,
0.16% by volume of $CO_x$,
45.8% by volume of $N_2$ and
1.64% by volume of $H_2O$.

The desired propylene conversion could no longer be maintained by increasing $T^{mean}$ within the limits of what the catalyst could withstand.

H) Example 7

The composition of the gas mixture 2 was:
0.05% by volume of 1-butene,
6.16% by volume of propylene,
33.0% by volume of propane,
12.3% by volume of oxygen,
0.16% by volume of $CO_x$,
46.7% by volume of $N_2$ and
1.70% by volume of $H_2O$.

| | |
|---|---|
| $A^{AA}$ = 85.1 mol % | $T^{mean}$, 1st reactor = 318° C. |
| $S^{COx}$ = 10 mol % | $T^{mean}$, 2nd reactor = 281° C. |

I) Example 8

The composition of the gas mixture 2 was:
0.09% by volume of 1-butene,
6.16% by volume of propylene,
32.9% by volume of propane,
12.3% by volume of oxygen,
0.15% by volume of $CO_x$,
46.8% by volume of $N_2$ and
1.68% by volume of $H_2O$.

| | |
|---|---|
| $A^{AA}$ = 85.0 mol % | $T^{mean}$, 1st reactor = 320° C. |
| $S^{COx}$ = 10.2 mol % | $T^{mean}$, 2nd reactor = 287° C. |

J) Example 9

The composition of the gas mixture 2 was:
0.20% by volume of 1-butene,
6.19% by volume of propylene,
32.7% by volume of propane,
12.3% by volume of oxygen,
0.18% by volume of $CO_x$,
46.7% by volume of $N_2$ and
1.71% by volume of $H_2O$.

The desired propylene conversion could no longer be maintained by increasing $T^{mean}$ within the limits of what the catalyst could withstand.

We claim:

1. A process for preparing at least one of a partial oxidation product and a partial ammoxidation product of propylene, in which
   a) in a first step, crude propane is subjected to at least one dehydrogenation of the group consisting of homogeneous dehydrogenation, homogenous oxydehydrogenation, heterogeneously catalyzed dehydrogenation and heterogeneously catalyzed oxydehydrogenation, in the presence of oxygen, in the absence of oxygen, or both in the presence and absence of oxygen to give a gas mixture 1 comprising propane and propylene, and
   b) part of the constituents other than propane and propylene present in the gas mixture 1 formed in the first step is, if appropriate, separated off from the gas mixture 1 and/or converted into other compounds so as to produce a gas mixture 1' comprising propane and propylene and also compounds other than oxygen, propane and propylene from the gas mixture 1 and, in at least one further step,
   c) at least one of gas mixture 1 and gas mixture 1' as constituent of a gas mixture 2 is subjected to at least one of a heterogeneously catalyzed gas-phase partial oxidation and a partial gas-phase ammoxidation of the propylene present in at least one of the gas mixture 1 and the gas mixture 1', to form at least one of acrolein, acrylic acid, propylene oxide and acrylonitrile,
   wherein the 1-butene content of the gas mixture 2 is $\leq 1\%$ by volume.

2. A process as claimed in claim 1, wherein the 1-butene content of the gas mixture 2 is $\leq 0.75\%$ by volume.

3. A process as claimed in claim 1, wherein the 1-butene content of the gas mixture 2 is $\leq 0.5\%$ by volume.

4. A process as claimed in claim 1, wherein the 1-butene content of the gas mixture 2 is $\leq 0.3\%$ by volume.

5. A process as claimed in claim 1, wherein the 1-butene content of the gas mixture 2 is $\leq 0.1\%$ by volume.

6. A process as claimed in claim 1, wherein the 1-butene content of the gas mixture 2 is $\geq 0.003\%$ by volume.

7. A process as claimed in claim 1, wherein the 1-butene content of the gas mixture 2 is $\geq 0.001\%$ by volume.

8. A process as claimed in any of claims 1 to 7, wherein the trans-2-butene content of the gas mixture 2 is $\leq 1\%$ by volume.

9. A process as claimed in any of claims 1 to 7, wherein the trans-2-butene content of the gas mixture 2 is $\leq 0.5\%$ by volume.

10. A process as claimed in any of claims 1 to 7, wherein the trans-2-butene content of the gas mixture 2 is $\leq 0.05\%$ by volume.

11. A process as claimed in claim 1, wherein the cis-2-butene content of the gas mixture 2 is $\leq 1\%$ by volume.

12. A process as claimed in claim 1, wherein the cis-2-butene content of the gas mixture 2 is $\leq 0.5\%$ by volume.

13. A process as claimed in claim 1, wherein the cis-2-butene content of the gas mixture 2 is $\leq 0.05\%$ by volume.

14. A process as claimed in claim 1, wherein the isobutene content of the gas mixture 2 is $\leq 1\%$ by volume.

15. A process as claimed in claim 1, wherein the isobutene content of the gas mixture 2 is $\leq 0.5\%$ by volume.

16. A process as claimed in claim 1, wherein the isobutene content of the gas mixture 2 is $\leq 0.05\%$ by volume.

17. A process as claimed in claim 1, wherein the total content of butenes in the gas mixture 2 is $\leq 1\%$ by volume.

18. A process as claimed in claim 1, wherein the total content of butenes in the gas mixture 2 is $\leq 0.5\%$ by volume.

19. A process as claimed in claim 1, wherein the total content of butenes in the gas mixture 2 is $\leq 0.05\%$ by volume.

20. A process as claimed in claim 1, wherein the total content of $C_4$-hydrocarbons in the gas mixture 2 is $\leq 3\%$ by volume.

21. A process as claimed in claim 1, wherein the total content of $C_4$-hydrocarbons in the gas mixture 2 is $\leq 2\%$ by volume.

22. A process as claimed in claim 1, wherein the total content of $C_4$-hydrocarbons in the gas mixture 2 is $\leq 1\%$ by volume.

23. A process as claimed in claim 1, wherein the total content of $C_4$-hydrocarbons in the gas mixture 2 is $\geq 0.05$ and is $\leq 3\%$ by volume.

24. A process as claimed in claim 1, wherein the gas mixture 1' contains $\geq 0.1\%$ by volume of constituents other than propane and propylene and oxygen.

25. A process as claimed in claim 1, wherein the gas mixture 1' contains ≧0.2% by volume of constituents other than propane and propylene and oxygen.

26. A process as claimed in claim 1, wherein the gas mixture 1' contains ≧0.3% by volume of constituents other than propane and propylene and oxygen.

27. A process as claimed in claim 1, wherein the gas mixture 1' contains ≧0.5% by volume of constituents other than propane and propylene and oxygen.

28. A process as claimed in claim 1, wherein the gas mixture 1' contains ≧1% by volume of constituents other than propane and propylene and oxygen.

29. A process as claimed in claim 1, wherein the gas mixture 1' contains ≧3% by volume of constituents other than propane and propylene and oxygen.

30. A process as claimed in claim 1, wherein the gas mixture 1' contains ≧5% by volume of constituents other than propane and propylene and oxygen.

31. A process as claimed in claim 1, wherein the gas mixture 1' contains ≧10% by volume of constituents other than propane and propylene and oxygen.

32. A process as claimed in claim 1, wherein the gas mixture 1' contains ≧30% by volume of constituents other than propane and propylene and oxygen.

33. A process as claimed in claim 1, wherein the gas mixture 2 contains up to 60% by volume of propane.

34. A process as claimed in claim 1, wherein the gas mixture 2 contains up to 50% by volume of propane.

35. A process as claimed in claim 1, wherein the gas mixture 2 contains from 20 to 40% by volume of propane.

36. A process as claimed in claim 1, wherein the gas mixture 2 comprises
from 7 to 15% by volume of $O_2$,
from 5 to 10% by volume of propylene,
from 15 to 40% by volume of propane,
from 25 to 60% by volume of nitrogen,
from 1 to 5% by volume of the total of CO, $CO_2$ and $H_2O$ and
from 0 to 5% by volume of other constituents, with any ammonia present being disregarded.

37. A process as claimed in claim 1, wherein the gas mixture 2 comprises
$H_2O$≦60% by volume,
$N_2$≦80% by volume,
$O_2$>0, ≦20% by volume,
CO≦2% by volume,
$CO_2$≦5% by volume,
ethane≦10% by volume,
ethylene≦5% by volume,
methane≦5% by volume,
propane>0, ≦50% by volume,
cyclopropane≦0.1% by volume,
propyne≦0.1% by volume,
propadiene≦0.1% by volume,
propylene<0, ≦30% by volume,
$H_2$≦30% by volume,
isobutane≦3% by volume,
n-butane≦3% by volume,
trans-2-butene≦1% by volume,
cis-2-butene≦1% by volume,
1-butene≦1% by volume,
isobutene≦1% by volume,
1,3-butadiene≦1% by volume,
1,2-butadiene≦1% by volume,
1-butyne≦0.5% by volume and
2-butyne≦0.5% by volume, with any ammonia present being disregarded.

38. A process as claimed in claim 1, wherein the crude propane contains ≧0.25% by volume of constituents other than propane and propylene.

39. A process as claimed in claim 1 wherein the crude propane contains ≧1% by volume of constituents other than propane and propylene.

40. A process as claimed in claim 1, wherein the crude propane contains ≧2% by volume of constituents other than propane and propylene.

41. A process as claimed in claim 1, wherein the crude propane contains ≧3% by volume of constituents other than propane and propylene.

42. A process as claimed in claim 1, wherein the crude propane contains up to 6% by volume of $C_4$-hydrocarbons.

43. A process as claimed in claim 1, wherein the crude propane contains from 0.1 to 6% by volume of $C_4$-hydrocarbons.

44. A process as claimed in claim 1, wherein the crude propane contains up to 0.5% by volume of 1-butene.

45. A process as claimed in claim 1, wherein the crude propane contains from 5 ppm by volume to 0.5% by volume of 1-butene.

46. A process as claimed in claim 1, wherein the crude propane contains a total of up to 0.5% by volume of butenes.

47. A process as claimed in claim 1, wherein the crude propane contains a total of from 5 ppm by volume to 0.5% by volume of butenes.

48. A process as claimed in claim 1, wherein the crude propane meets the following specification:
propane content ≧90% by volume,
total content of propane and propylene ≦99% by volume,
total content of $C_4$-hydrocarbons ≦6% by volume,
1-butene content ≦0.5% by volume,
total content of butenes ≦0.5% by volume,
ethane content ≦10% by volume,
ethylene content ≦5% by volume,
methane content ≦5% by volume,
cyclopropane content ≦0.1% by volume,
propylene content ≦10% by volume,
total content of $C_3$-hydrocarbons other than propane and propylene ≦0.3% by volume,
total content of $C_5$-hydrocarbons ≦0.3% by volume,
and total content of $C_6$–$C_8$-hydrocarbons ≦600 ppm by volume.

49. A process as claimed in claim 1, wherein the propane conversion in the first step is from ≧5 mol % to ≦30 mol %.

50. A process as claimed in claim 1, wherein the partial oxidation and/or ammoxidation product or products of propylene is/are separated off from the product gas mixture from the gas-phase partial oxidation and/or partial gas-phase ammoxidation and at least the unreacted propane present in this product gas mixture is recirculated to the first step and/or to the gas-phase partial oxidation and/or partial gas-phase ammoxidation.

51. A process as claimed in claim 1, wherein the process of the present invention is carried out in a reaction zone over a catalyst charge whose active composition consists of at least one multimetal oxide composition comprising the elements Mo, V, at least one of the two elements Te and Sb and at least one element selected from the group consisting of Nb, Ta, W, Ti, Al, Zr, Cr, Mn, Ga, Fe, Ru, Co, Rh, Ni, Pd, Pt, La, Bi, B, Ce, Sn, Zn, Si, Na, Li, K, Mg, Ag, Au and In in combination.

52. A process as claimed in claim 51, wherein the active composition consists of at least one multimetal oxide composition which has the element stoichiometry I $$Mo_1V_bM^1_cM^2_d \qquad (I),$$

where
M¹=Te and/or Sb,
M²=at least one element from the group consisting of Nb, Ta, W, Ti, Al, Zr, Cr, Mn, Ga, Fe, Ru, Co, Rh, Ni, Pd, Pt, La, Bi, Ce, Sn, Zn, Si, Na, Li, K, Mg, Ag, Au and In,
b=0.01 to 1,
c=>0 to 1 and
d=>0 to 1.

53. A process as claimed in claim 52, wherein M¹=Te and M²=Nb, Ta, W and/or Ti.

54. A process as claimed in claim 52, wherein M²=Nb.

55. A process as claimed in claim 51, wherein the X-ray diffraction pattern of the active multimetal oxide composition or compositions displays reflections h and i whose maxima are at the diffraction angles 22.2±0.5° (h) and 27.3±0.5° (i).

56. A process as claimed in claim 55, wherein the X-ray diffraction pattern additionally displays a reflection k whose maximum is at 28.2±0.5°.

57. A process as claimed in claim 55, wherein the reflection h is the most intense in the X-ray diffraction pattern and has a width at half height of not more than 0.5°.

58. A process as claimed in claim 57, wherein the width at half height of the reflection i and of the reflection K is in each case ≦1° and the intensity $P_k$ of the reflection k and the intensity $P_i$ of the reflection i fulfill the relationship 0.20≦R≦0.85, where R is the intensity ratio defined by the formula $$R=P_i/(P_i+P_k).$$

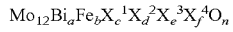

59. A process as claimed in claim 51, wherein the X-ray diffraction pattern of the active multimetal oxide composition or compositions displays no reflection whose maximum is at 2Θ=50±0.3°.

60. A process as claimed in claim 1, wherein the first step is carried out in a separate reaction zone.

61. A process as claimed in claim 60, wherein the first step is a heterogeneously catalyzed dehydrogenation.

62. A process as claimed in claim 60, wherein a part comprising at least one $C_4$-hydrocarbon of the constituents other than propane and propylene present in the gas mixture 1 is separated off from the gas mixture 1.

63. A process as claimed in claim 60, wherein a part comprising at least one butene of the constituents other than propane and propylene present in the gas mixture 1 is separated off from the gas mixture 1.

64. A process as claimed in claim 60, wherein a part comprising at least 1-butene of the constituents other than propane and propylene present in the gas mixture 1 is separated off from the gas mixture 1.

65. A process as claimed in claim 60, wherein the heterogeneously catalyzed gas-phase partial oxidation and/or partial gas-phase ammoxidation is carried out using a catalyst whose active composition comprises the elements Mo, Bi and Fe.

66. A process as claimed in claim 60, wherein the heterogeneously catalyzed gas-phase partial oxidation and/or partial gas-phase ammoxidation is carried out using a catalyst whose active composition is a multimetal oxide of the formula IV $$Mo_{12}Bi_aFe_bX_c^1X_d^2X_e^3X_f^4O_n \qquad (IV),$$

where the variables have the following meanings:
X¹=nickel and/or cobalt,
X²=thallium, an alkali metal or an alkaline earth metal, c, phosphorus, arsenic, boron, antimony, tin, cerium, lead and/or tungsten,
X⁴=silicon, aluminum, titanium and/or zirconium,
a=0 to 5,
b=0.01 to 5,
c=0 to 10,
d=0 to 2,
e=0 to 8,
f=0 to 10 and
n=a number determined by the valence and abundance of the elements other than oxygen in (IV).

67. A process as claimed in claim 60, wherein the heterogeneously catalyzed gas-phase partial oxidation is carried out using a catalyst whose active composition comprises the elements Mo and V.

68. A process as claimed in claim 60, wherein the heterogeneously catalyzed gas-phase partial oxidation is carried out using a catalyst whose active composition is a multimetal oxide of the formula VII $$Mo_{12}V_aX_b^1X_c^2X_d^3X_e^4X_f^5X_g^6O_n \qquad (VII),$$

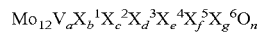

where the variables have the following meanings:
X¹=W, Nb, Ta, Cr and/or Ce,
X²=Cu, Ni, Co, Fe, Mn and/or Zn,
X³=Sb and/or Bi,
X⁴=one or more alkali metals,
X⁵=one or more alkaline earth metals,
X⁶=Si, Al, Ti and/or Zr,
a=1 to 6,
b=0.2 to 4,
c=0.5 to 18,
d=0 to 40,
e=0 to 2,
f=0 to 4,
g=0 to 40 and
n=a number determined by the valence and abundance of the elements other than oxygen in VII.

69. A process as claimed in claim 1, wherein the partial oxidation and/or ammoxidation product or products of propylene comprise(s) at least one compound from the group consisting of propylene oxide, acrolein, acrylic acid and acrylonitrile.

70. A process as claimed in claim 1, wherein a first step comprises subjecting crude propane to a heterogeneously catalyzed dehydrogenation in the presence and/or absence of oxygen and subjecting gas mixture 1 to a heterogeneously catalyzed gas phase ammoxidation of propylene present in the gas mixture 1.

71. A process as claimed in claim 1, wherein a first step comprises subjecting crude propane to a heterogeneously catalyzed dehydrogenation in the presence and/or absence of oxygen and also in the presence of water vapor and condensing all or some of the water vapor out of the gas mixture 1 formed in the first step to obtain a gas mixture 1' which is subjected to a heterogeneously catalyzed gas phase partial oxidation and/or partial gas phase ammoxidation of propylene present in the gas mixture 1'.

72. A process as claimed in claim 1, wherein a first step comprises subjecting crude propane to a heterogeneously catalyzed dehydrogenation which is autothermal.

73. A process as claimed in claim 1, wherein the gas mixture 1 and/or gas mixture 1' are subjected as a constituent of a gas mixture 2 to a heterogeneously catalyzed partial gas phase ammoxidation of propylene present in the gas mixture 1 and/or gas mixture 1'.

* * * * *